United States Patent
Wittwer et al.

(10) Patent No.: US 10,494,682 B2
(45) Date of Patent: Dec. 3, 2019

(54) METHODS OF DETECTING COPY NUMBER VARIATION

(71) Applicants: Carl Wittwer, Salt Lake City, UT (US); Luming Zhou, Salt Lake City, UT (US); Robert Palais, Salt Lake City, UT (US)

(72) Inventors: Carl Wittwer, Salt Lake City, UT (US); Luming Zhou, Salt Lake City, UT (US); Robert Palais, Salt Lake City, UT (US)

(73) Assignees: The University of Utah Research Foundation, Salt Lake City, UT (US); Utah Valley University, Orem, UT (US)

( * ) Notice: Subject to any disclaimer, the term of this patent is extended or adjusted under 35 U.S.C. 154(b) by 622 days.

(21) Appl. No.: 14/757,825

(22) Filed: Dec. 23, 2015

(65) Prior Publication Data
US 2016/0153058 A1 Jun. 2, 2016

Related U.S. Application Data

(63) Continuation of application No. PCT/US2014/044154, filed on Jun. 25, 2014.

(60) Provisional application No. 61/839,269, filed on Jun. 25, 2013.

(51) Int. Cl.
| | |
|---|---|
| C12P 19/34 | (2006.01) |
| C12Q 1/70 | (2006.01) |
| C12Q 1/6876 | (2018.01) |
| C12Q 1/6883 | (2018.01) |
| C12Q 1/6886 | (2018.01) |
| G01N 21/64 | (2006.01) |
| G01N 25/04 | (2006.01) |

(52) U.S. Cl.
CPC .......... *C12Q 1/703* (2013.01); *C12Q 1/6876* (2013.01); *C12Q 1/6883* (2013.01); *C12Q 1/6886* (2013.01); *G01N 21/6486* (2013.01); *G01N 25/04* (2013.01); *C12Q 2600/112* (2013.01); *C12Q 2600/124* (2013.01); *C12Q 2600/158* (2013.01)

(58) Field of Classification Search
CPC ........ C12Q 2527/107; C12Q 2527/137; C12Q 1/6827; C12Q 1/686; C12Q 2531/113; C12Q 1/6876; C12Q 1/6883; C12Q 1/6886; C12Q 1/703; C12Q 2600/112; C12Q 2600/124; C12Q 2600/158; G01N 21/6486; G01N 25/04
USPC ...................................................... 435/91.2
See application file for complete search history.

(56) References Cited

U.S. PATENT DOCUMENTS

| | | | |
|---|---|---|---|
| 8,068,992 B2 | 11/2011 | Palais et al. | |
| 8,296,074 B2 | 10/2012 | Palais et al. | |
| 2006/0281099 A1 | 12/2006 | Breneman et al. | |
| 2008/0020390 A1 | 1/2008 | Mitchell et al. | |
| 2010/0120038 A1* | 5/2010 | Mir ...................... | C12Q 1/6853 435/6.1 |
| 2010/0267109 A1 | 10/2010 | Rothberg et al. | |
| 2010/0285468 A1 | 11/2010 | Xin | |
| 2011/0041222 A1* | 2/2011 | Marchetti .......... | C12N 15/8216 800/317 |
| 2011/0223602 A1 | 9/2011 | Whitman et al. | |
| 2012/0258524 A1 | 10/2012 | Wittwer et al. | |
| 2012/0322058 A1 | 12/2012 | Regan et al. | |
| 2013/0260447 A1* | 10/2013 | Link ....................... | G01N 1/38 435/287.2 |

FOREIGN PATENT DOCUMENTS

| | | |
|---|---|---|
| WO | 1995020676 A1 | 8/1995 |
| WO | 2004038038 A2 | 5/2004 |
| WO | 2012038503 A1 | 3/2012 |
| WO | 2014210199 A | 12/2014 |

OTHER PUBLICATIONS

Lorenz., Journal of Visualized Experiments, 63, e3998, 1-15, May (Year: 2012).*
D'haene et al., Methods, 50: 262-270 (Year: 2010).*
PCT/US2014/044154, International Search Report and Written Opinion, dated Jan. 6, 2015, 24 pages.
PCT/US2014/044154, International Preliminary Report on Patentability, dated Jan. 7, 2016, 15 pages.
PCT/US2014/044154, Invitation to Pay Add'l Fees and Partial Search Report, dated Oct. 20, 2014, 2 pages.
Sample & Assay Technologies Critical Factors for Successful Real-Time PCR 2, http://www.gene-quantification.com/qiagen-qpcr-sample-assay-tech-guide-2010.pdf, Jul. 2010, 64 pages.
14816610.1, et al., Supplementary European Search Report, dated Jan. 26, 2017, 10 pages.
Hung,Chia-Cheng et al., Quantitative and Qualitative Analyses of the SNRPN Gene Using Real-Time PCR with Melting Curve Analysis, The Journal of Molecular Diagnostics, vol. 13, No. 6, Nov. 2011, 5 pages.
Lang,Alois H. et al., Optimized Allele-Specific Real-Time PCR Assays for the Detection of Common Mutations in KRAS and BRAF, The Journal of Molecular Diagnostics, vol. 13, No. 1, Jan. 2011, 6 pages.
Markoff,A. et al., Reduced allele specific annexin A5 mRNA levels in placentas carrying the M2/ANXA5 allele, Placenta 31, 2010, pp. 937-940.
Wang,Wen et al., Detection and Discrimination between Deletional and Non-Deletional Prader-Willi and Angelman Syndromes by Methylation-Specific PCR and Quantitative Melting Curve Analysis, Journal of Molecular, vol. 11, No. 5, Sep. 2009, 4 pages.

(Continued)

*Primary Examiner* — Cynthia B Wilder
(74) *Attorney, Agent, or Firm* — Stoel Rives LLP

(57) ABSTRACT

Methods and kits for performing polymerase chain reaction (PCR) and melting analyses to determine copy number variation and/or gene expression are disclosed herein. Related uses of such methods and analyses are also disclosed herein.

21 Claims, 23 Drawing Sheets

Specification includes a Sequence Listing.

(56) References Cited

OTHER PUBLICATIONS

Chinese Intellectual Property Office, First Office Action and Search Report dated Aug. 10, 2017 in Chinese Patent Application No. 201480036694.2.

Agata, et al., "Large genomic deletions inactivate the BRCA2 gene in breast cancer families", J Med Genet vol. 42, 2005, 6 pages.

Algars, et al., "EGFR gene copy numbers assessment from areas with highest EGFR expression predicts response to anti-EGFR therapy in colorectal cancer", British Journal of Cancer vol. 105, 2011, pp. 255-262.

Borun, et al., "Comparative-high resolution melting: a novel method of simultaneous screening for small mutations and copy number variations", Human Genetics 133, 2014, pp. 535-545.

Cunningham, et al., "Cetuximab monotherapy and cetuximab plus irinotecan in irinotecan-refractory metastatic colorectal cancer", New England Journal of Medicine vol. 351, Jul. 22, 2004, pp. 337-345.

Dahabreh, et al., "EGFR gene copy number as a predictive biomarker for patients receiving tyrosine kinase inhibitor treatment: a systematic review and meta-analysis in non-small-cell lung cancer", Annals of Oncology vol. 22, Sep. 8, 2011, pp. 545-552.

D'Haene, et al., "Accurate and objective copy number profiling using real-time quantitative PCR", Methods vol. 50, 2010, pp. 262-270.

Dobrowolski, et al., "Newborn screening for spinal muscular atrophy by calibrated short-amplicon melt profiling", Clin Chem. vol. 58, Jun. 2012, pp. 1033-1039.

Erali, et al., "SNP genotyping by unlabeled probe melting analysis", Methods in Molecular Biology, vol. 429, 2008, pp. 199-206.

George, et al., "False-positive diagnosis of trisomy 21 using fluorescence in situ hybridisation (FISH) on uncultured amniotic fluid cells", Prenatal Diagnosis, vol. 23, 2003, pp. 302-305.

Gonzalez, et al., "The influence of CCL3L1 gene-containing segmental duplications on HIV-1/AIDS susceptibility", Science vol. 307, Mar. 4, 2005, pp. 1434-1440.

Guo, et al., "Rapid Diagnosis of Aneuploidy by High-Resolution Melting Analysis of Segmental Duplications", Clinical Chemistry 58:6, Molecular Diagnostics and Genetics, 2012, pp. 1019-1025.

Hartmann, et al., "Large BRCA1 gene deletions are found in 3% of German high-risk breast cancer families", Human Mutation vol. 24, 2004, 8 pages.

Hirsch, et al., "Combination of EGFR gene copy number and protein expression predicts outcome for advanced non-small-cell lung cancer patients treated with gefitinib", Annals of Oncology vol. 18, Feb. 22, 2007, pp. 752-760.

Huik, et al., "CCL3L1 copy number is a strong genetic determinant of HIV seropositivity in Caucasian intravenous drug users", Journal of Infectious Diseases vol. 201, Mar. 1, 2010, pp. 730-739.

Ingham, et al., "Quantitative real-time PCR assay for determining transgene copy number in transformed plants", Biotechniques vol. 31, 2001, pp. 132-139.

International Human Genome, "Finishing the euchromatic sequence of the human genome", Nature vol. 431, 2004, pp. 931-945.

Janssen, et al., "MLPA analysis for the detection of deletions, duplications and complex rearrangements in the dystrophin gene: potential and pitfalls", Neurogenetics 6, 2005, pp. 29-35.

Komura, et al., "Genome-wide detection of human copy number variations using high-density DNA oligonucleotide arrays", Genome Res 16, 2006, pp. 1575-1584.

Lai, et al., "Comparative analysis of algorithms for identifying amplifications and deletions in array CGH data", Bioinformatics 21, 2005, pp. 3763-3770.

Palais, et al., "Mathematical algorithms for high-resolution DNA melting analysis", Methods Enzymol 454, 2009, pp. 323-343.

Paxton, et al., "Rapid aneusomy detection in products of conception using the KaryoLite BACs-on-Beads assay", Prenatal Diagnosis vol. 33, 2013, pp. 25-31.

Petrij-Bosch, et al., "BRCA1 genomic deletions are major founder mutations in Dutch breast cancer patients", Nature Genetics vol. 17, Nov. 1997, pp. 341-345.

Press, et al., "Numerical Receipes: The Art of Scientific Computing", Third Edition, Cambridge University Press, 2007, 3 pages.

Quemener, et al., "Complete ascertainment of intragenic copy number mutations (CNMs) in the CFTR gene and its implications for CNM formation at other autosomal loci", Human Mutation vol. 31, 2010, pp. 421-428.

Schneider, et al., "Large deletions in the CFTR gene; clinics and genetics in Swiss patients with CF", Clinical Genetics vol. 72, 2007, pp. 30-38.

Schouten, et al., "Relative quantification of 40 nucleic acid sequences by multiplex ligation-dependent probe amplification", Nucleic Acids Research, vol. 30, No. 12, 2002, 13 pages.

Sepulveda, et al., "A Poisson hierarchical modelling approach to detecting copy number variation in sequence coverage data", BMC Genomics vol. 14, 2013, 12 pages.

Sharp, et al., "Segmental duplications and copy-number variation in the human genome", American Journal of Human Genetics vol. 77, 2005, pp. 78-88.

Stankiewicz, et al., "Structural Variation in the Human Genome and its Role in Disease", Annual Review of Medicine vol. 61, 2010, pp. 437-455.

Urban, et al., "High-resolution mapping of DNA copy alterations in human chromosome 22 using high-density tiling oligonucleotide arrays", Proc Natl Acad Sci USA, vol. 103, No. 12, Mar. 21, 2006, pp. 4534-4539.

Visakorpi, et al., "Sensitive detection of chromosome copy number aberrations in prostate cancer by fluorescence in situ hybridization", American Journal of Pathology, vol. 145, No. 3, Sep. 3, 1994, pp. 624-630.

Vossen, et al., "High-Resolution Melting Analysis (HRMA)—More Than Just Sequence Variant Screening", Official Journal Human Genome Variation Society, Human Mutation, vol. 30, No. 6, 2009, pp. 860-866.

Wang, et al., "High EGFR copy number predicts benefits from tyrosine kinase inhibitor treatment for non-small cell lung cancer patients with wild-type EGFR", Journal of Translational Medicine, vol. 11, 2013, 10 pages.

Wittwer, et al., "High-Resolution DNA Melting Analysis: Advancements and Limitations", Official Journal Human Genome Variation Society, Human Mutation, Vo. 30, No. 6, 2009, pp. 857-859.

Xi, et al., "Copy number variation detection in whole-genome sequencing data using the Bayesian information criterion", Proc Natl Acad Sci USA vol. 108, No. 46, Nov. 15, 2011, pp. E1128-1136.

\* cited by examiner

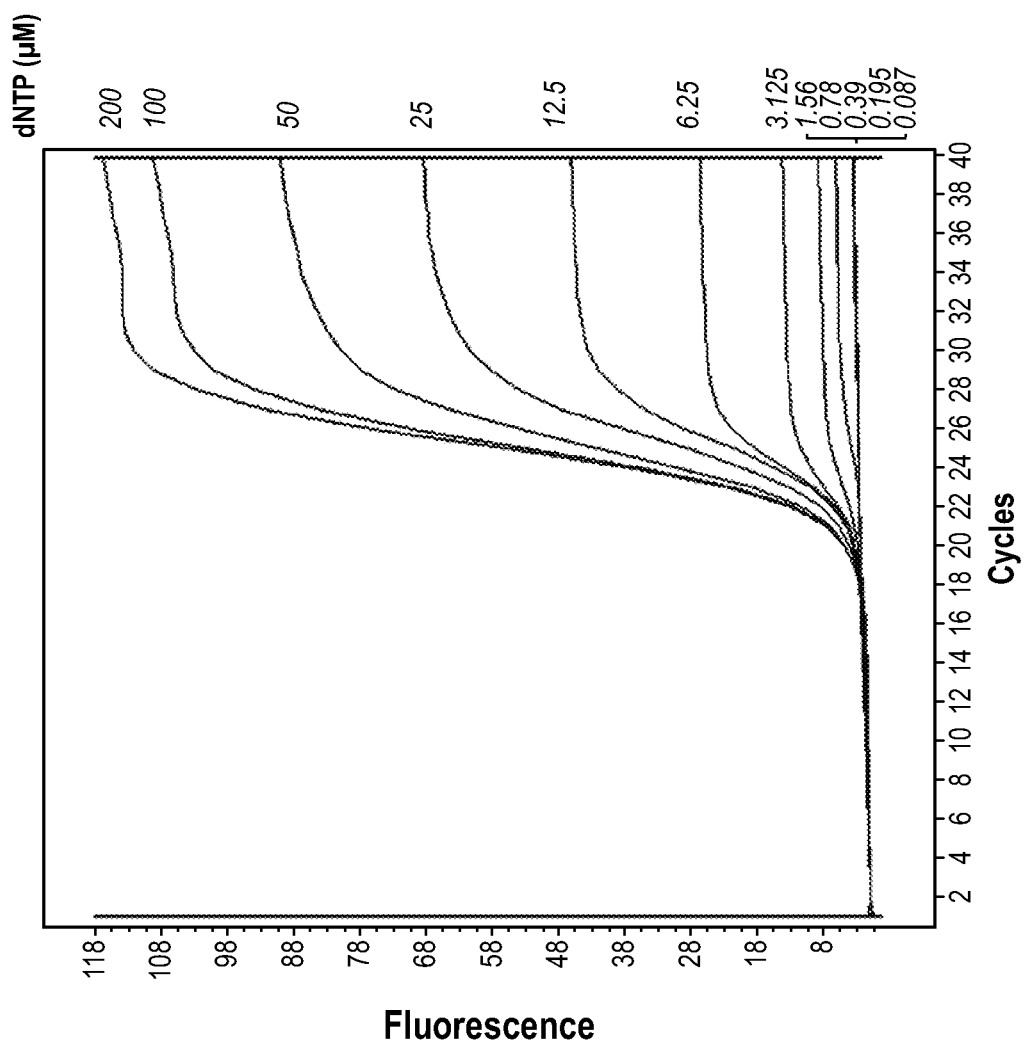

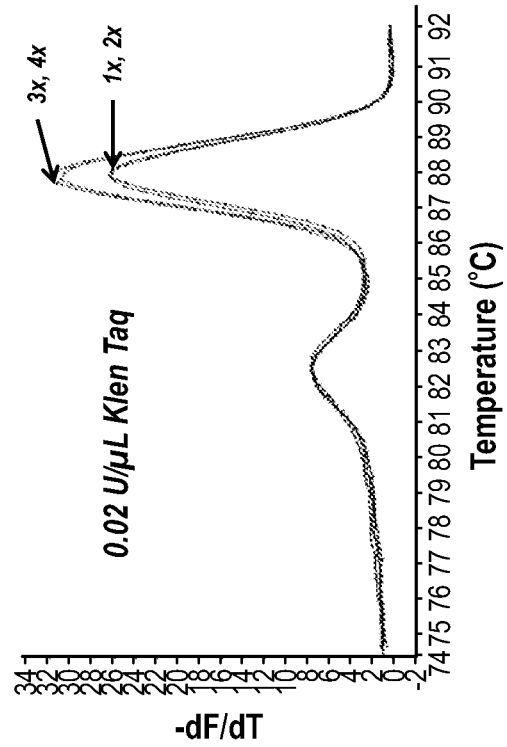
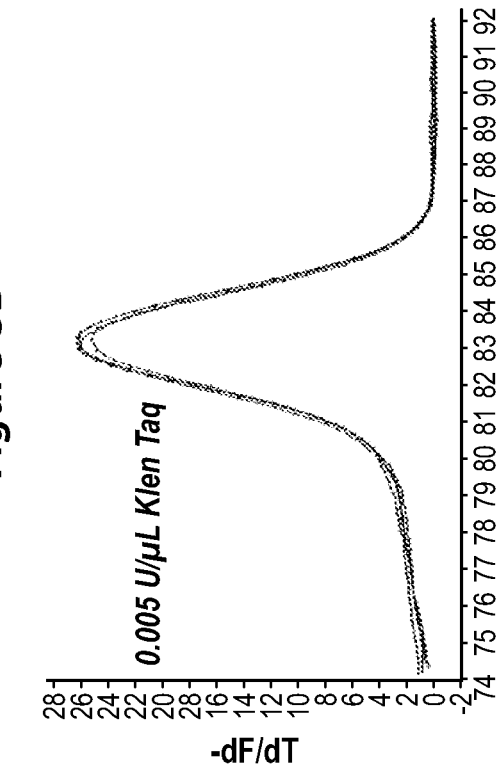
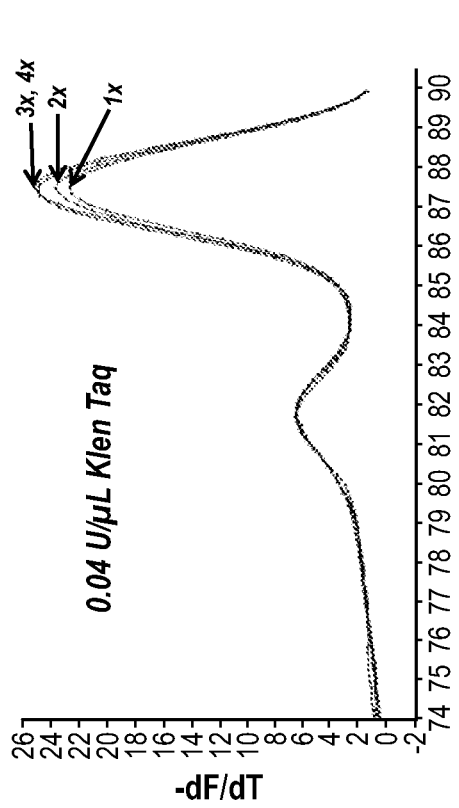
Figure 5A, Figure 5B, Figure 5C, Figure 5D

*Figure 10*

| Name | SEQUENCE | | PRODUCT | |
|---|---|---|---|---|
| | Forward primer | Reverse primer | Size (bp) | Tm (°C) |
| CFTRx7F (SEQ ID NO:1) | TTGTGATTACCTCAGAAATGATTGA | | 68 | 77 |
| CFTRx7R (SEQ ID NO:2) | | CATTGCTTCTTCCCAGCAGT | | |
| Ch13-104895F (SEQ ID NO:3) | AACGGGAGGGGTGTATGTTT | | 82 | 84 |
| Ch13-104895R (SEQ ID NO:4) | | GCAGACTAGGTGCCCAACTT | | |
| 18TPGS2x4F (SEQ ID NO:5) | ACATCATTCCACTGGGAAGC | | 99 | 84 |
| 18TPGS2x4R (SEQ ID NO:6) | | CCAGAGTGGGTGCATTAGGA | | |
| 21S11F (SEQ ID NO:7) | TCAGACTTGGACAGCCACAC | | 109 | 84 |
| 21S11R (SEQ ID NO:8) | | CACTTGGGGAATTGACTCACA | | |
| CYBBx10F (SEQ ID NO:9) | CCTTCAGGATAGCGGTTGAT | | 121 | 87 |
| CYBBx10R (SEQ ID NO:10) | | CTTGAGAATGGATGCGAAGG | | |
| SRYF (SEQ ID NO:11) | CAACAGGTTGTACAGGGATGA | | 60 | 82 |
| SRYR (SEQ ID NO:12) | | AGCTGGTGCTCCATTCTTGA | | |
| CFx6F (SEQ ID NO:13) | CTCCTCATGGGGCTAATCTG | | 54 | 82.5 |
| CFx6R (SEQ ID NO:14) | | AAGTCCACAGAAGGCAGACG | | |
| 21FTCDx6F (SEQ ID NO:15) | AGCCAGGTTCTTCTCATCCA | | 61 | 83 |
| 21FTCDx6R (SEQ ID NO:16) | | GCCAGGACGTCTGAAGAAAG | | |
| CFx2F (SEQ ID NO:17) | TCTGTTGATTCTGCTGACAATCT | | 50 | 73 |
| CFx2R (SEQ ID NO:18) | | TGAACATACCTTTCCAATTTTCA | | |
| CFx3F (SEQ ID NO:19) | GGGATAGAGAGCTGGCTTCA | | 54 | 77 |
| CFx3R (SEQ ID NO:20) | | GCCGAAGGGCATTAATGAGT | | |
| EGFRx20F (SEQ ID NO:21) | ATGTCCGGGAACACAAAGAC | | 80 | 84 |
| EGFRx20R (SEQ ID NO:22) | | TCCCTTCCCTGATTACCTTTG | | |
| CFx24-2F (SEQ ID NO:23) | CCCTCCGACAGGGTGAA | | 151 | 87 |
| CFx24-2R (SEQ ID NO:24) | | AGCAAATGTCCCATGTCAAC | | |
| T40-1F (SEQ ID NO:25) | TCATTCTCGTTTTCTGAACTG | | 100 | 81 |
| T40-1R (SEQ ID NO:26) | | ATGTTTAGACTGGATAGCGT | | |
| SMAF (SEQ ID NO:27) | TTCCTTTATTTTCCTTACAGGGTTT | | 50 | 74.5 |
| SMA1R (SEQ ID NO:28) | | CCTTCCTTCTTTTTGATTTTGTCTG | | |
| SMAF (SEQ ID NO:27) | TTCCTTTATTTTCCTTACAGGGTTT | | 50 | 73.7 |
| SMA2R (SEQ ID NO:29) | | CCTTCCTTCTTTTTGATTTTGTCTA | | |

METHODS OF DETECTING COPY NUMBER VARIATION

RELATED APPLICATIONS

This application is a continuation of International Patent Application No. PCT/US2014/044154, filed Jun. 25, 2014, and published as WO 2014/210199, and claims the benefit of U.S. Provisional Patent Application No. 61/839,269, filed Jun. 25, 2013; the contents of all of which are hereby incorporated by reference herein in their entirety.

TECHNICAL FIELD

The present disclosure relates generally to polymerase chain reaction (PCR). More specifically, the present disclosure relates to methods of limiting PCR and performing melt analyses and uses of such methods and analyses.

BACKGROUND

Deoxyribonucleic acid (DNA) copy number variation (CNV) is associated with certain genetic disorders, chromosomal rearrangements, and cancers.

The standard method for detection of CNV used routinely in the clinical lab is fluorescent in situ hybridization (FISH) [13,14]. The resolution of FISH is about 100 kilobases (kb), but CNVs involving shorter segments are difficult to detect with this method. In the last decade after completion of the human genome sequence [15], several molecular detection techniques capable of resolving shorter CNVs have revealed a remarkable degree of structural variation present among normal individuals.

The most popular techniques developed in the last decade are Comparative Genomic Hybridization (CGH) arrays, Single Nucleotide Polymorphism (SNP) arrays, real-time quantitative PCR (qPCR) and Multiplex Ligation-dependent Probe Amplification (MLPA) and massively parallel sequencing. Array-based techniques (CGH array and SNP array) are efficient for global and high resolution scans of structural features of human genome-wide variation [16-19]. The resolution of high density targeted arrays has approached to a few base pairs. In recent years, next-generation sequencing has been used for CNV detection [20,21]. The above methods are time consuming and require costly equipment and reagents.

Real-time qPCR can be used to calculate CNVs from the change in threshold crossing cycle number ($\Delta\Delta Cq$) [22,23]. This approach is rapid and needs no expensive instruments. Commonly observed ratios of copy number variations in the human genome can be 10:1 or greater, or as small as 4:3. The 3:2 ratios involved in trisomy (e.g., Down syndrome) are especially common. In theory, qPCR can be used to detect 2:1 CNVs and even trisomies, but considerable care is required in practice for reliable results, and it is very difficult to distinguish the smaller ratios by qPCR. qPCR is generally used for gene expression, however, for copy number determination, qPCR has been less used in the clinic.

MLPA has been widely used to detect CNVs associated with genetic disease in the clinical laboratory because it can detect large deletions and duplications in genes (typically deletions or duplications of exons) [24,25]. However, MLPA is time consuming and requires long customized oligonucleotide probes. All of these approaches, except real-time PCR, require at least one day to complete.

A need exists for rapid, alternative methods of determining CNVs and determining gene expression.

SUMMARY

Methods of limiting PCR and performing melting analyses are disclosed herein. These methods may be used for a variety of purposes, such as determining genetic copy number variations (CNVs) and determining relative expression level of genes.

For example, in some embodiments, the methods comprise amplifying of a region of interest (or locus) of a genetic sample using polymerase chain reaction (PCR) while limiting amplification. The methods may further comprise determining a melting curve of any resulting amplicons and then comparing the melting curve to a reference curve of a reference, wherein a difference between the two curves indicates the presence of a copy number variation in the region of interest of the genetic sample.

In another example, in some embodiments, the methods comprise amplifying a region of interest of a genetic sample and also amplifying a reference using polymerase chain reaction (PCR) while limiting amplification. The methods may further comprise determining a melting curve of the region of interest and a melting curve of the reference, and then comparing a melting peak of the region of interest to a melting peak of the reference, wherein a difference between the two peaks indicates a difference in relative copy number or expression levels.

Methods of analyzing PCR melting temperature data are also disclosed. The methods comprise performing PCR on a genetic sample and a reference. The methods further comprise acquiring raw fluorescence versus melting temperature data, such as with a LightScanner. The methods may comprise removing background noise from the raw fluorescence versus melting temperature data. The methods may further comprise normalizing all the melting temperature data, followed by normalizing the height of the reference fluorescence peaks to reveal differences in the genetic sample peaks.

Kits for performing such methods are also provided.

BRIEF DESCRIPTION OF THE DRAWINGS

FIG. 1A illustrates duplex amplification with different deoxyribonucleotide triphosphate (dNTP) concentrations.

FIG. 5A illustrates melting curves of PCR at standard polymerase concentration.

FIG. 5B illustrates melting curves of PCR at 0.2 U/μL polymerase concentration.

FIG. 5C illustrates melting curves of PCR at 0.1 U/μL polymerase concentration.

FIG. 5D illustrates melting curves of PCR at 0.05 U/μL polymerase concentration.

FIG. 10 lists the primers used in most of the examples herein. The size in base pairs and Tm describe the resultant amplicon.

DETAILED DESCRIPTION

Figure 1B:
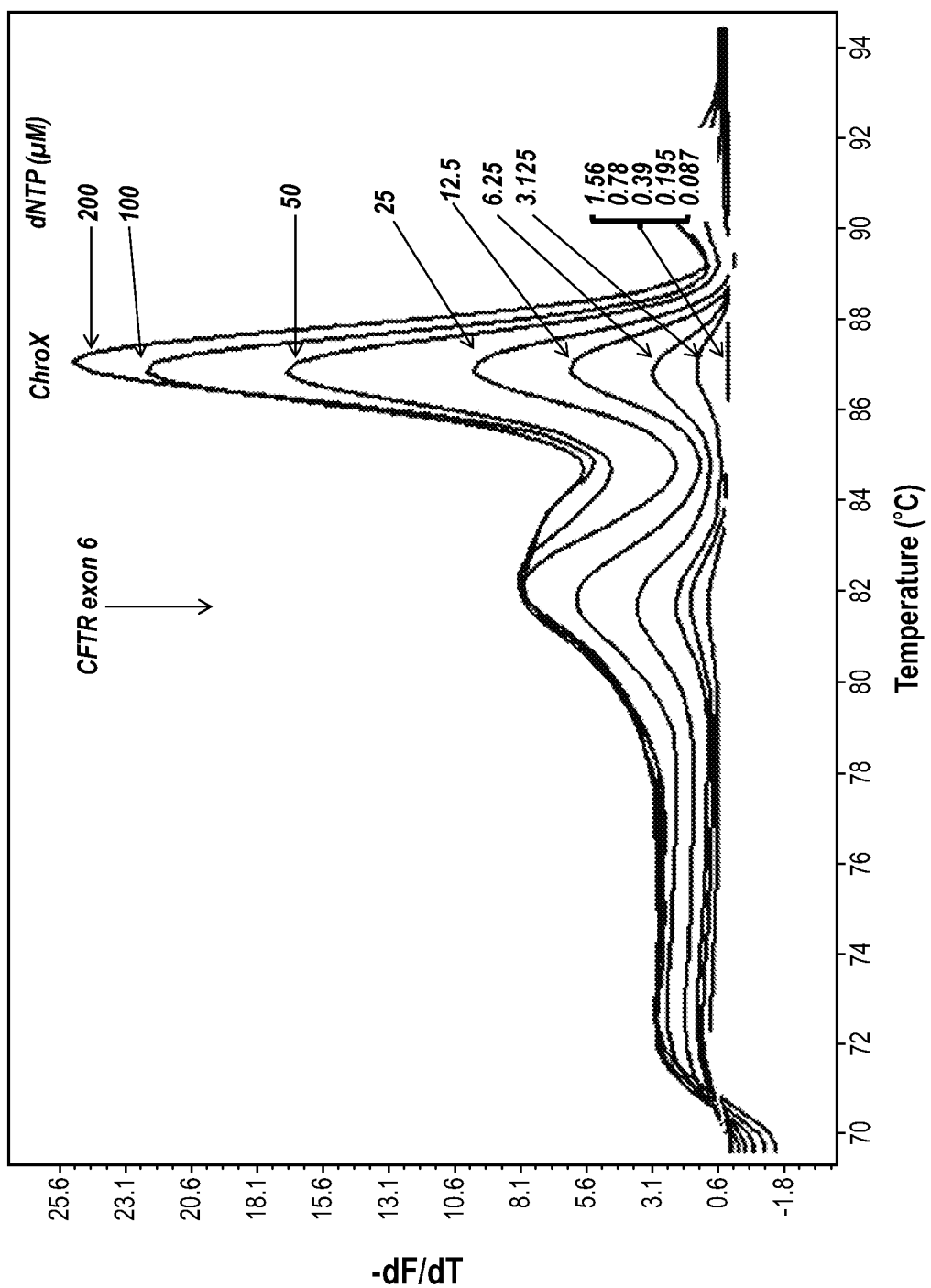
FIG. 1B illustrates melting curves of the duplex amplification illustrated in FIG. 1A.

Copy number variation (CNV) is a common type of genetic variation. About 13% of genes in the human genome have variation in copy number [1]. CNVs are associated with human disease and population diversity. CNVs can be caused by structural rearrangements of the genome such as deletions and duplications. Many genetic diseases are caused by the loss or gain of large segments of deoxyribonucleic acid (DNA) sequence. For example, 1-3% of cystic fibrosis cases are caused by decreased copy number due to a large deletion in the Cystic Fibrosis Transmembrane conductance Regulator (CFTR) gene [2,3]. Likewise, similar portions of breast cancer cases are caused by large deletions in breast cancer type 1 susceptibility gene (BRCAI) and breast cancer type 2 susceptibility gene (BRCAII) [4-6]. In another example, the CNV of entire chromosomes occur, such as in Trisomy 13, Trisomy 18, and Trisomy 21. Susceptibility to Human Immunodeficiency Virus (HIV) infection is associated with an increase in Chemokine (C—C motif) ligand 3-like 1 (CCL3L1) gene copy number [7,8]. For example, higher copy number of the epidermal growth factor receptor (EGFR) gene is related to colon cancer and non-small cell lung cancer [9-12].

Methods of determining genetic CNVs are disclosed herein. In some embodiments, the methods comprise amplifying a region of interest of a genetic sample using polymerase chain reaction (PCR), while limiting amplification of the region of interest. The methods may further comprise determining a melting curve of any resulting amplicons and then comparing the melting curve to a reference curve of a reference, wherein a difference between the two curves indicates the presence of a copy number variation.

Measuring the expression level of a gene in a particular cell, tissue, and/or organism may be important for any number of reasons. Methods of determining relative expression levels of genes are disclosed herein. The methods comprise amplifying a region of interest of a genetic sample and also amplifying a reference using polymerase chain reaction (PCR) while limiting amplification. The methods may further comprise determining a melting curve of the region of interest and of the reference and then comparing a melting peak of the region of interest to a melting peak of the reference, wherein a difference between the two peaks indicates a difference in relative expression levels.

Limiting amplification of the region of interest may comprise one or more of: (a) limiting a total number of PCR cycles prior to a plateau of amplification of the region of interest; (b) limiting an amount of deoxyribonucleotide triphosphate (dNTP) present during PCR sufficient to reduce amplification of the region of interest; or (c) limiting an amount of polymerase present during PCR sufficient to reduce amplification of the region of interest.

Under option (a), the PCR cycles may be limited to be about at a cycle at which an amplified region of interest is distinguishable from background noise also generated during the amplification, referred to herein as the "quantification cycle" or "Cq". In some embodiments, the PCR cycles may be limited to within plus or minus three cycles of the Cq. In some embodiments, the PCR cycles may be limited to within plus or minus two cycles of the Cq. In some embodiments, the PCR cycles may be limited to within plus or minus one cycle of the Cq. The PCR cycle that is the Cq may depend upon the initial template copy number. It may be necessary to determine the Cq for a sample before determining CNV under this approach.

Under option (b), the concentration of dNTPs prior to initiating PCR may be limited to about 30% standard PCR protocol concentration to about 1% standard PCR protocol concentration, including about 25%, about 12.5%, about 6.25%, about 3.125%, and about 1.56% standard PCR protocol concentration. For example, for a PCR protocol that normally would use a concentration of about 200 microMolar ($\mu$M) dNTPs prior to initiating PCR, which is a common standard PCR protocol concentration, then the concentration of dNTPs may be limited to be about 50 $\mu$M to about 3.1 $\mu$M, including about 25 $\mu$M, about 12.5 $\mu$M, and about 6.25 $\mu$M. While all four dNTPs are limited in the examples used herein, it is understood that one, two, or three dNTPs may be so limited, illustratively depending on GC content. Under option (c), the concentration of polymerase prior to initiating PCR may be limited to about 50% standard PCR concentration to about 20% standard PCR concentration, including about 25% standard PCR concentration. For example, for a PCR protocol that normally would use a polymerase concentration of about 0.04 U/$\mu$L, then the polymerase concentration may be about 0.02 U/$\mu$L or about 0.01 U/$\mu$L.

The methods of determining genetic CNVs may further comprise calculating a percent difference in copy number and/or a ratio of genetic sample copy number to reference. The methods of determining relative expression levels of genes may further comprise calculating a percent difference and/or a ratio of expression levels.

For the methods of determining genetic CNVs, the genetic sample may comprise nucleic acids such as deoxyribonucleic acids (DNA) or ribonucleic acids (RNA). For the methods of determining relative expression levels of genes, the genetic sample may comprise messenger ribonucleic acids (mRNA). When the sample comprises RNA, such as mRNA, then the methods may comprise performing reverse transcription of the genetic sample prior to the amplifying step.

In some embodiments of the methods, the PCR comprises end-point PCR. For example, end-point PCR may be used for either relative or absolute determination of genetic CNV's or relative expression level of genes.

In some embodiments of the methods, the PCR comprises real-time PCR.

The methods of determining genetic CNVs may further comprise amplifying a reference in the same reaction mixture as the region of interest. The reference may comprise a wild-type allele of the region of interest of the genetic sample. The reference may have an unknown amplification efficiency. The primers for the reference may be different or the same as the primers for the region of interest. The concentration of the primers for the reference and the primers for the region of interest may be the same or different.

For the methods of determining expression levels, the reference may comprise a housekeeping gene expressed in the same cell or tissue of the gene of the region of interest. The reference may have an unknown amplification efficiency. The primers for the reference may be different from the primers for the region of interest. The concentration of the primers for the reference and the primers for the region of interest may be the same or different.

In some embodiments of the methods, the region of interest of the genetic sample and reference amplicons may be chosen from regions having minimal single nucleotide polymorphisms (SNPs) and other sequence variants. If heterozygous mutations or SNPs are present on an amplicon of the region of interest or of the reference, the corresponding melting peak may be lower and wider or exhibit two peaks, and may degrade the detection accuracy. For the same reason, the region of interest and reference fragments may be chosen to exhibit single melting domains that will be easier to normalize to the reference melting peak. Two melting domains on a reference peak may not be too difficult to interpret, but if the region of interest fragment has two or more melting domains, then the signal may split among the peaks, and the determination of either relative expression level or copy number variation may be more difficult. In some embodiments, the amplicons may be designed so that both the region of interest and reference fragments each have one melting domain.

In some embodiments of the methods, during multiplex PCR, annealing and amplification efficiency may be different for different primers. This could affect the ratio of region of interest amplicons to reference amplicons as the reaction progresses and be a source of uncertainty in the results. Increasing the annealing time may be employed to equalize the efficiencies. The annealing time may be sufficiently limited in time to avoid amplification of a nonspecific product.

In some embodiments of the methods, the methods may comprise collecting hybridization fluorescence versus melting temperature data.

In some embodiments, the fluorescence is generated by a saturating dsDNA binding dye, such as LCGreen, LCGreen+, Syto9, EvaGreen, and ResoLight Dye, and other saturating dyes, as are known in the art, many of which are listed in U.S. Pat. No. 7,456,281, herein incorporated by reference. Fluorescence may also be generated by unsaturating dsDNA binding dyes, as are known in the art. The most commonly used unsaturating dsDNA binding dye is SYBR Green I, while other commonly used unsaturating dsDNA binding dyes are listed in Table 1 of U.S. Pat. No. 7,582,429, also incorporated by reference. It is understood that in homozygous genotypes, it may be desirable to use a saturating dsDNA binding dye, to take advantage of precision that can be provided by such dyes. In heterozygous genotypes, an unsaturating dye may be preferred, as heterozygous genotypes may produce a low-temperature peak or shoulder from the mismatches that occur, and the redistribution of the unsaturating dye may minimize such a low-temperature peak or shoulder. However, the specific choice of dye may depend on the exact assay being performed. In some embodiments, the fluorescence may be generated by a labeled probe, such as molecular beacons, hybridization probes, TaqMan probes, Scorpion probes, LNA (Locked Nucleic Acid) probes, and cycling probes.

In certain embodiments, it may be desirable to amplify only one allele. In ARMS PCR (or PCR amplification of specific alleles (PASA)), one of the primers is designed in such a way that it is able to discriminate among templates that differ by a single nucleotide residue located at the 3'-end of that primer. Only that sequence that matches the 3'-end of the primer is extended efficiently. Thus, an ARMS primer can be designed to amplify a specific member of a multi-allelic system while remaining refractory to amplification of another allele that may offer by as little as a single base from the non-complementary allele. Other methods of amplifying a single allele are known and are contemplated herein.

While PCR is the amplification method used in the examples herein, it is understood that any amplification method that limits the amplification plateau by limiting the number of cycles, the amount of polymerase or other appropriate enzyme, or the amount of dNTPs or NTPs, may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based helicase-dependant amplification (HDA); transcription-mediated amplification (TMA), and the like. Therefore, when the term PCR is used, it should be understood to include other alternative amplification methods.

High-resolution melting analysis may be performed on the collected fluorescence versus melting temperature data. The high-resolution melting analysis may optionally include normalizing the data both in terms of temperature and fluorescent intensity. Comparing the melting curve of the region of interest to the reference curve of the reference nucleic acid may comprise normalizing the melting peaks and observing difference in the peak height or area of melting curves in the region of interest. See U.S. Pat. No. 7,582,429, herein incorporated by reference. However, because the negative derivative is used in determining peak heights, normalization may not be necessary.

In some embodiments of the methods of determining CNVs, the relative copy number is quantified. In other embodiments, an absolute quantity is quantified. For absolute quantification, the genetic sample concentration may be standardized. Also for absolute quantifications, the reference may not be amplified with the genetic sample and the reference may comprise a calibration curve.

In some embodiments of the methods, multiple regions of interest of the same genetic sample may be amplified in the same PCR. In such embodiments, the primers for each of the regions of interest may be different from each other and preferentially have the same or similar primer Tms. However, the amplicon Tms illustratively should be separated from each other by 4-10 degrees Centigrade. Although product melting temperatures can be closer than 4 degrees Centigrade (for example 1-2 degrees C.), the peaks may begin to overlap and it can be more difficult to assign accurate peak heights or areas to each product. Multiple Gaussian curves can be fit to the overlapping peaks to better estimate the heights or areas, but it is simpler to avoid the problem if it is possible to separate the melting peaks. Particularly problematic is when the reference and target copy numbers are very different, say 10:1 and the Tms are close. There may not even be a peak in the derivative melting plot to identify, although multiple Gaussian fitting might reveal the presence of the minor peak.

The methods of determining genetic CNVs can detect CNVs using DNA melting analysis by simply limiting concentration of dNTPs, DNA polymerase, cycle number (or a combination) in the PCR reaction. The methods may be substantially simpler, faster, and more economical and/or accurate than current state-of-the-art methods that are utilized to quantify copy number variation. Additionally, there may be no need to adjust templates or modify or design specialized oligonucleotides. The methods disclosed herein may be performed using any PCR platform having integrated melting or a PCR platform along with a separate melting instrument (e.g., LightScanner). For some embodiments, real-time PCR is not necessary, but may be used. Only five to ten minutes may be required to implement the method after PCR. Given the many serious conditions that are associated with CNV, such an improvement of the technology for detecting and quantifying CNV may be highly beneficial. The method may also be used to confirm the presence of a copy number variation after it is presumptively detected by a whole genome method (CNV array, SNP array, or next generation sequencing)

A method of detecting a birth defect in a fetus is also disclosed. The method comprises using one of the methods of determining genetic CNVs disclosed above and comprises using a genetic sample that comprises fetal DNA. In some embodiments, the fetal DNA may be obtained from maternal serum.

A method of detecting a genetic disorder is also disclosed. The method comprises using one of the methods of determining genetic CNVs disclosed above.

A method of determining cancer type is also disclosed. The method comprises using one of the methods of determining genetic CNV disclosed above and comprises using a genetic sample from tissue suspected to be cancerous. For example, colon cancer and/or lung cancer may be identified, depending upon the presence of particular CNVs.

A method of determining susceptibility to Human Immunodeficiency Virus (HIV) infection in a patient is also disclosed. The method comprises using one of the methods of determining genetic CNVs disclosed above, wherein the region of interest of the genetic sample comprises a portion of the Chemokine (C—C motif) ligand 3-like 1 (CCL3L1) gene of the patient.

A method of determining a degree of viral infection is also disclosed. The method comprises using one of the methods of determining genetic CNV disclosed above and comprises using a genetic sample from virally-infected tissue. The method may further comprise using armored viruses as a reference.

Methods of analyzing polymerase chain reaction (PCR) melting temperature data are also disclosed. The methods comprise performing PCR on at least one genetic locus and a reference gene. The methods further comprise acquiring raw fluorescence versus melt temperature data. The methods comprise removing background noise from the raw fluorescence versus melting temperature data. The methods further comprise normalizing the remaining melt temperature data and then normalizing the reference fluorescence peaks to compare the peak height or area of the genetic locus peaks.

Removing background noise may comprise performing exponential background subtraction, although other methods of removing background noise are contemplated.

Optional shifting or overlay of the remaining melt temperature data may comprise shifting each of the resulting curves to minimize a least-squares separation between the curves. The shifting may comprise determining the mean temperature of each curve over a particular interval and shifting each curve by the difference between its individual mean and the average of all curve means. The particular interval may be temperature data corresponding to a fluorescent intensity of about 5% to about 15% of peak intensity. The particular interval may be a region of high temperature and low hybridization that is transitioning from exponentially decreasing hybridization, such as the right-hand-most "ankle-shaped" region of a negative derivative plot of fluorescence versus temperature melt data.

In other embodiments, the reference peak may serve not only as a fluorescence intensity normalizer that allows the genetic locus peaks or areas to be compared, but also as an internal temperature control to correct for slight temperature differences between samples due to position on an amplification plate or buffer differences. The reference peak then serves 2 functions: a fluorescence intensity normalizer, and a temperature adjuster in order to obtain more precise curves for comparison.

In some embodiments, normalizing the remaining melting temperature data may utilize other norms than the least squares separation between the curves, such as, for example, the maximum or mean absolute value, root mean square, derivatives, and/or the $L^p$ with p=infinity, 1, and 2. The selected norm could also be weighted near the middle, lower, or upper fluorescent intensity or temperature range. Additionally, each norm could be applied to discrete data rather than to data that has been fit. The normalization may be selected so as to minimize the separation of known conserved features of the region of interest and reference peaks (or other peaks included in the reaction) where separation is defined by any mathematical quantity satisfying the properties of a norm or distance function.

In some embodiments, normalizing the remaining melt temperature data may comprise amplifying one or two internal controls with the genetic sample. The difference between the actual and expected peak temperature for the internal control may be to scale the peak temperatures of the region of interest.

The methods may further comprise calculating the negative derivative of the temperature-normalized data prior to normalizing the reference fluorescence intensity peaks to compare the genetic sample peaks.

In other embodiments, the methods may comprise removing background noise by performing a nonlinear least-squares fit to an exponential, $Ce^{\{rt\}}$, using the Levenberg-Marquart method. The resulting exponential decay factor "r" as a function of the (mean) temperature of the points in the fitting window may be used instead of the negative derivative of the melting curve. Systems and methods for removing background noise are provided in PCT Publication No. WO2007/035806, filed on Sep. 20, 2006, and entitled, "MELTING CURVE ANALYSIS WITH EXPONENTIAL BACKGROUND SUBTRACTION," and PCT Publication No. WO2010/132813, filed on May 14, 2010, and entitled, "SYSTEMS AND METHODS FOR AUTOMATED MELTING CURVE ANALYSIS," the contents of each of which is hereby incorporated by reference in its entirety.

The methods may further comprise performing unbiased hierarchal clustering on the normalized fluorescence peaks. Methods of performing unbiased hierarchal clustering known in the art may be used, such as those disclosed in Reference 27 cited herein [27].

The methods may also further comprise quantifying relative copy number by locating target peaks of the normalized fluorescence peaks, performing a least squares fit, and calculating the ratios of the peaks. Additionally or alternatively, ratios of curve areas may also be used. Likewise, the methods may also be used to quantify relative expression levels.

EXAMPLES

The results of studies testing the effects of varying cycle number, dNTPs, and polymerase to limit amplification on the resolution of copy number ratio quantification are presented first, according to the particular parameter that was varied. The blinded tests, experiments with 10-fold sample volume variation, higher multiplex, heterozygous deletion detection, and SYBR Green experiments are presented next, as they were based on using methods and parameters obtained from the earlier experiments. Experiments illustrating the use of the methods disclosed herein for determining relative expression levels of genes are presented last.

Genomic samples with 1, 2, 3, and 4 copies of chromosome X provided useful template for studies of CNV detection methods. The percentage difference between 1 and 2 copies is 50%, 2 and 3 copies is 33%, and 3 and 4 copies is 25%. In the examples below, the human cell line genomic DNA samples were purchased from Coriell Institute for Medical Research. Sample NA11472 is male DNA with the standard one copy of chromosome X. Sample NA18800 is female DNA with the standard 2 copies of chromosome X. Sample NA03623 contains 3 copies of chromosome X. Sample NA11226 contains 4 copies of chromosome X. Sample NA18668 has heterozygous deletions in CFTR exon 2 and exon 3. Fifty genomic DNA samples, some exhibiting each of trisomy 13, 18, 21 as well as wild-type, and another 50 samples exhibiting monosomy, triploid syndrome, as well as wild-type were provided by ARUP laboratories. The genomic DNA was extracted directly from residual cleaned villi, fetal somatic tissue or decidua using 5 Prime DNA extraction reagents (Fisher Scientific, Pittsburgh, Pa.). All DNA samples' copy number variants had been detected by Affymetrix SNP 6.0 microarray [26].

In the examples below, uMelt software (dna.utah.edu/umelt/umelt.html) was used to predict melting curves and melting temperatures (Tms) of copy number variant (CNV) and reference amplicons. The Tm difference between the region of interest (target) amplicon and reference amplicon was designed to be between 2° C. and 10° C. Human genome databases (www.ncbi.nlm.nih.gov and genome.ucsc.edu) were searched to confirm that the target and reference sequences occur uniquely in the human genome, and that the probability of sequence variation was minimal.

In the examples below, the reference and target fragments were selected as follows:

A fragment of Cystic Fibrosis Transmembrane conductance Regulator (CFTR) exon 7 on chromosome 7 was chosen as reference for CNV detection of chromosomes 13, 18, 21, X, and Y. A fragment of CFTR exon 6 on chromosome 7 was selected as the reference for CNV of chromosome X alone. A fragment of Cytochrome b-245 beta (CYBB) exon 10 was also used as reference for CNVs of chromosome X. A fragment of the Sex-determining Region Y (SRY) was used for CNVs of chromosome Y. A fragment of MIM 104895 (NCBI gene bank number) was used to detect CNV of chromosome 13. A fragment of Tubulin PolyGlutamylase complex Subunit 2 (TPGS2) exon 4 was used in CNV analysis of chromosome 18. A fragment near the microsatellite marker D21S11 was used with chromosome 21. A fragment of FormiminoTransferase Cyclo-Deaminase (FTCD) exon 6 on chromosome 21 was used as reference for CFTR exon 2 and exon 3 deletions. The primer sequences of the reference and targets are shown in FIG. 10.

In examples below, multiplex PCR involving either two or three amplicons followed by high-resolution melting analysis was used to detect CNV or relative gene expression. In the examples below, one constituent is always the reference, along with either one or two targets. Unless stated otherwise below, the PCR reagents included 0.04 U/μL KLENTAQ1™ (Ab Petides) with 64 ng antiTaq antibody (eEnzyme), 2 mM Mg++, 50 mmol/L mM Tris (pH 8.3), 1× LCGREEN® PLUS (BioFire Diagnostics), 0.5 μm of each primer. Different concentrations of genomic DNA from 5 ng to 200 ng and different concentrations of dNTPs were used to compare and optimize assays for quantification. The PCR was performed in 10 μL volumes.

After completion of PCR, high resolution melting was performed to quantify the melting peak ratio of reference and target. Duplex PCRs were used to detect trisomy 13, 18 and 21. Triplex PCR was used to simultaneously detect CNVs of chromosome X and Y by comparing their corresponding CNV melting peaks with the reference peak. Triplex PCR was also used to detect heterozygous deletions in CFTR exon 2 and 3.

PCR was performed on the LightCycler 480 (Roche). Following an initial denaturation at 95° C. for 2 minutes, each cycle included 10 s denaturation at 95° C., 30 s annealing at 65° C., and 10 s extension at 72° C., to plateau. Each high-resolution melting acquisition as described above, was performed at a ramp rate 0.04° C./s from 65° C. to 95° C. with 15 acquisitions/° C. Annealing temperatures 1-2° C. higher than the primer Tms were used. A high annealing temperature reduces the probability of nonspecific amplification. A long annealing time increases similarity of primer annealing efficiency so that the results are more accurate and shorter amplicons are not preferentially amplified. However, this amplification protocol is illustrative only, and it is understood that other amplification protocols may be used.

In the examples below, several transformations were applied to the raw high-resolution melting (fluorescence vs. temperature) data to accurately identify and quantify copy number ratios and relative gene expression. In the first step, the hybridization vs. temperature curve was extracted using exponential background subtraction [27]. In the second step, individual shifts of the temperature domain were applied to each of the resulting curves to minimize a least-squares separation between curves in a low hybridization interval, $[p_L,p_H]=[0.05,0.15]$, that exhibits conserved features independent of sample. The shifts were obtained by finding the mean temperature of each curve in this interval, after which each curve is shifted by the difference between its individual mean, and the average of all curve means. The mean temperature of a curve was found by extracting points $(t_j,p_j)$ of the curve whose hybridization were in the [0.05,0.15] interval and then reversing their independent and dependent variables to make temperature the dependent variable, $(p_j,t_j)$. These points were fit using the minimum least squares polynomial of degree n=2, also known as the n=2 Savitzky-Golay or simply SG2 fit of the form $T(p)=ap^2+bp+c$ [28]. The mean temperature used in shifting was the integral mean of T(p) over the interval $[p_L,p_H]$: $[a(p_H^3-p_L^3)/3+b(p_H^2-p_L^2)/2+c(p_H-p_L)]/(p_H-p_L)$. In the third step, the negative derivative of the shifted curves were calculated by performing a SG2 fit of the form $p(T)=aT^2+bT+c$ of the shifted curves in a sliding window, [T,T+W]. Points on the negative derivative curve were obtained by evaluating the negative derivative of the fit at the mean <T> of the points in each window: $(<T>, -p'(<T>)=-(2a<T>+b))$. In the fourth step, a portion of the reference peak of each curve above a threshold fraction of their maximum were extracted and again the SG2 fit of the form $p(T)=aT^2+bT+c$ was calculated. The amplitude of the vertex, $p(-b/(2a))$ was calculated after which each curve was scaled by the ratio of the reference peak amplitude to the average of all peak amplitudes.

Alternatively, instead of curve overlay or temperature shifting as described in the second step above, temperature adjustments on each curve are made at the end by determining the maximum temperature of the reference peak by setting the first derivative of $p(T)=aT^2+bT+c$ as described above to zero (2aT+b=0; T=−b/2a). Then, each curve is horizontal shifted to the main maximum T of all curves.

Illustratively, when the temperature scale is adjusted so that the location of corresponding reference peaks agree, such is done additively to preserve the relative separation of signal peaks. Thus, the natural choice of temperature to which they will be adjusted is the additive, or arithmetic mean. This is defined as the single number that can be added to itself in place of several different numbers to obtain the same sum. For example, the additive mean of 2, 5, and 11 is 6, because 2+5+11=18=6+6+6. This is often referred to as the average. Therefore, the additive mean of the n numbers denoted a_1, a_2, . . . , a_n is 1/n (a_1+a_2+ . . . +a_n).

When the dye signal scale is adjusted (illustratively, after background removal), so that the height of corresponding reference peaks agree, such may done multiplicatively, so as to preserve the relative heights of signal peaks. Thus, the natural choice of Signal (negative derivative) Peak height to which they will be adjusted is the multiplicative, or geometric mean. This is defined as the single number that can be multiplied by itself in place of several different numbers to obtain the same product. For example, the multiplicative mean of 3,8, and 9 is 6, because 3*8*9=216=6*6*6. Therefore, the multiplicative mean of the n numbers denoted a_1, a_2, . . . , a_n is (a_1*a_2* . . . *a_n)^(1/n), where the 1/n power signifies the n-th root of the product in parentheses.

Note that it may be desirable to preserve the significance of zero signal (derivative) peak, corresponding to constant absolute signal from constant dye interaction with hybridized DNA. This requires the multiplicative rather than additive adjustment. One might ask whether the same requirement on temperature is required for preserving absolute zero temperature. However, in the temperature scale of the experiment, the appropriate model for temperature error is a homogeneous shift due to differences in acquired experimental temperature at different locations in a plate, or due to changes in specifics of single sample instruments from one run to the next.

Thus, as used herein, melting curves may mean raw fluorescence vs temperature, or adjusted by background subtraction, or derivative peaks, with or without shifting or adjustment, or any combination. It is understood that such processing of the melting data depends on the application.

Samples were classified into copy number variant classes by performing unbiased hierarchal clustering on the rescaled target peaks. Relative copy number was quantified by locating target peaks of the rescaled curves, performing one more SG2 fit of the form $p(T)=aT^2+bT+c$, and calculating the ratios of the vertex amplitudes, $p(-b/(2a))$. Relative gene expression was similarly calculated.

Example 1—Varying Cycle Number Study

Figure 2A:
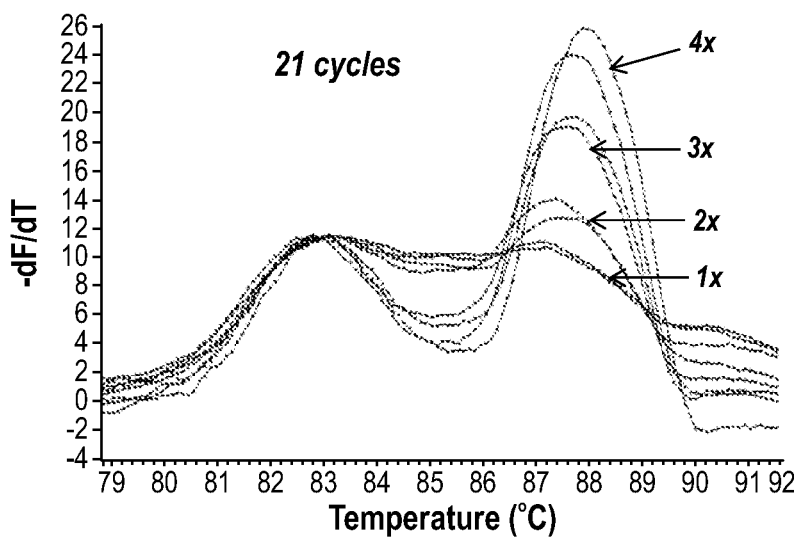
FIG. 2A illustrates polymerase chain reaction (PCR) amplification stopped at 21 cycles.
Figure 2B:
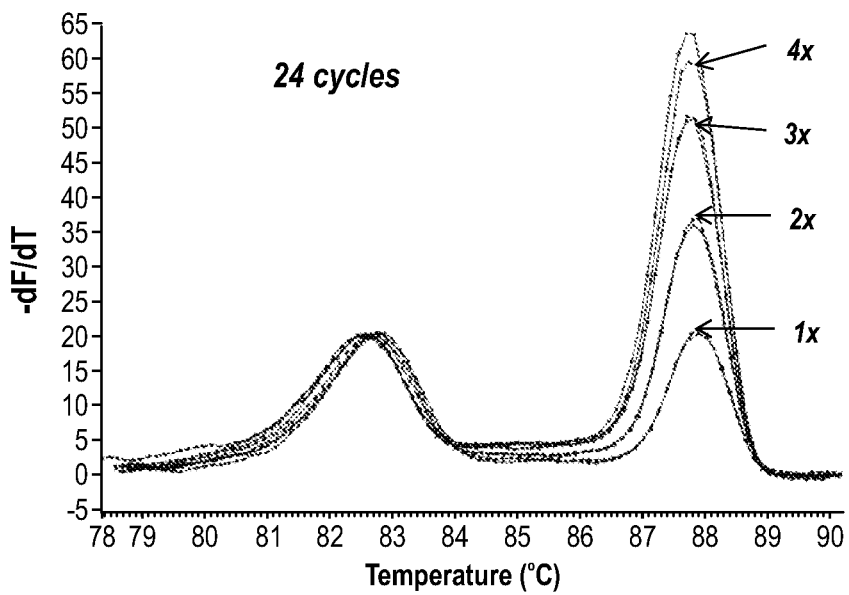
FIG. 2B illustrates PCR amplification stopped at 24 cycles.
Figure 2C:
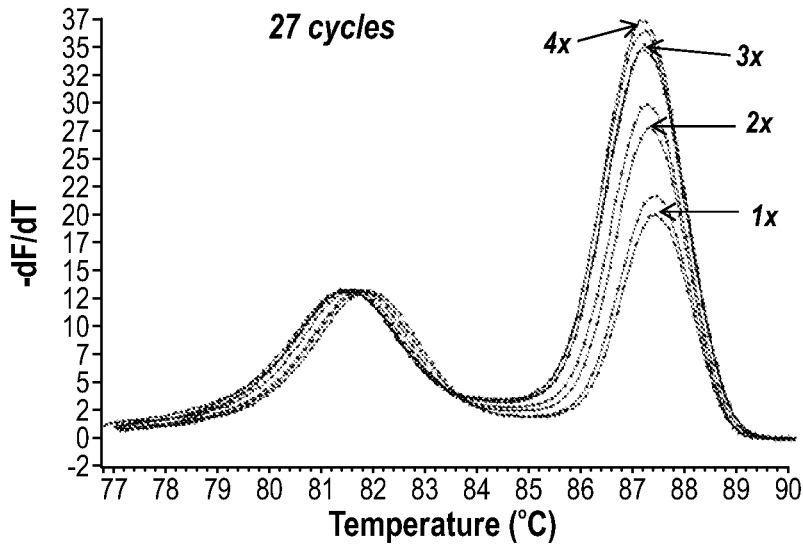
FIG. 2C illustrates PCR amplification stopped at 27 cycles.
Figure 2D:
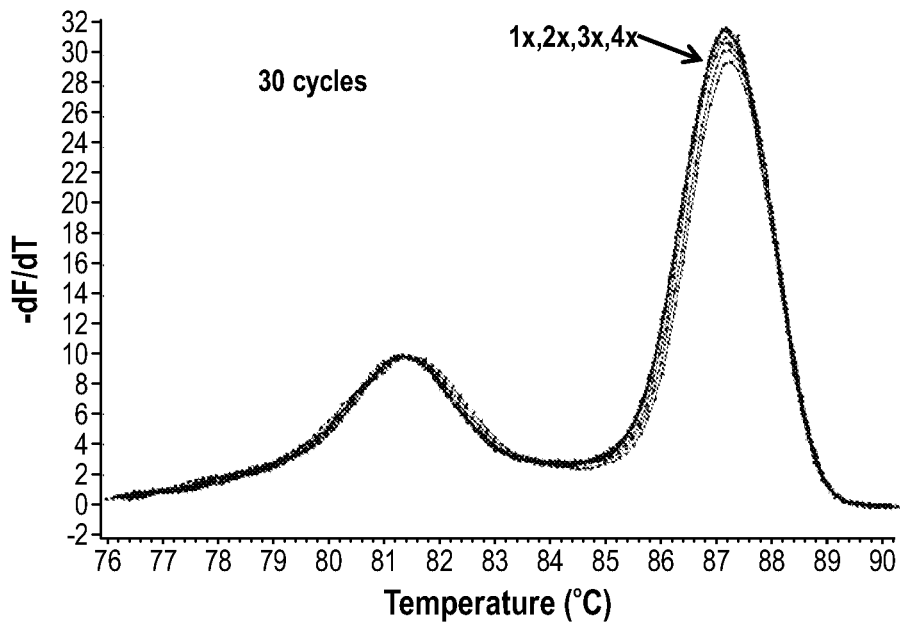
FIG. 2D illustrates PCR amplification stopped at 30 cycles.
Figure 2E:
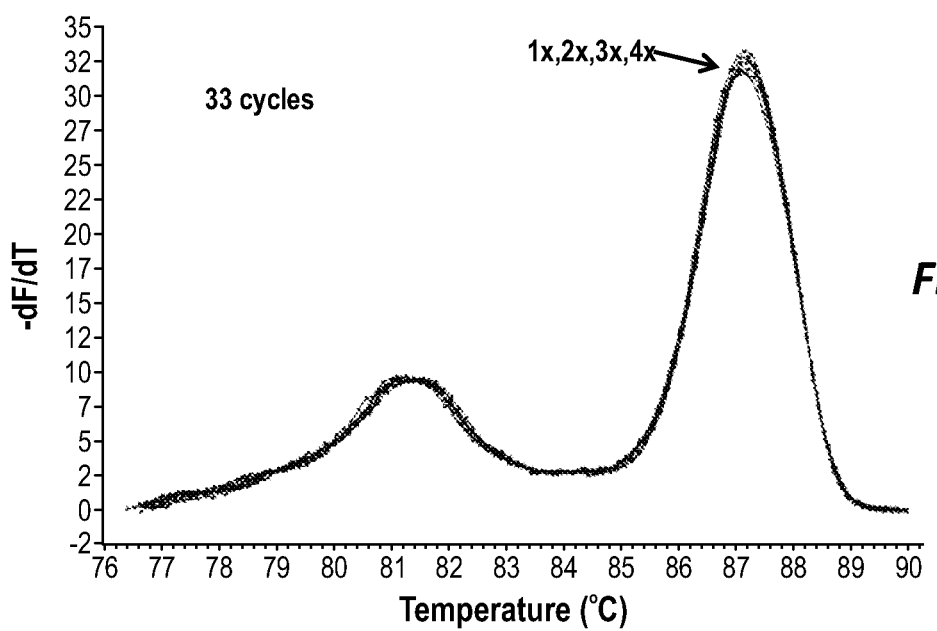
FIG. 2E illustrates PCR amplification stopped at 33 cycles.

A standard PCR was performed to establish a benchmark for comparison. Using a standard PCR concentration of KlenTaq1 (0.04 U/μL) and dNTP (200 μM each), PCR reached plateau after 35 cycles with Cq on average just before the 24$^{th}$ cycle (23.8). The PCRs were stopped at different cycles before and after Cq, and melting was performed and peaks compared. When the PCR stopped at 18$^{th}$ cycle, no amplicon melting peaks were visible (data not shown). When the PCR stopped at the 21$^{st}$ cycle (pre-Cq), the 4 different copies of chromosome X were distinguishable but the PCR melting peaks of CNV and reference were very low (FIG. 2A). When the PCR stopped at the 24$^{th}$ cycle (at Cq), the 4 different copy numbers of chromosome X were distinguished well and melting peak signals were strong, with ratios of CNVs to reference the same as in the genomic template (FIG. 2B). When PCR was stopped after the 27$^{th}$ cycle (post Cq), more primers were consumed and the 3 copies and 4 copies chromosome X were barely distinguishable from each other (FIG. 2C). Therefore, the sensitivity of CNV detection drops to 33% (the 3:2 case). When the PCR was stopped at the $30^{th}$ or $33^{rd}$ cycle (almost before or after plateau), again more primers were consumed and all 4 different copy numbers of chromosome X were indistinguishable (FIGS. 2D and 2E). By the 30th or 33rd cycle, the reference and CNV amplicon ratio may reflect the ratio of primers rather than the initial genomic template ratios.

When limiting by cycle number, the Cq cycle appeared the best for limiting PCR to detect CNV by melting. The sensitivity of the ability to distinguish CNV by this method is at least 25% (the 4:3 case).

If the template concentrations are different, the Cqs may be different, causing the CNV ratio detection from Cq to potentially be inaccurate. Using this approach, reactions should be allowed to progress to their own Cq, not a fixed cycle number, or variation in initial concentration may place that cycle before or after the reactions Cq and potentially degrade the accuracy of CNV ratio determination from peaks.

From the experiments of this Example 1, when PCR is stopped at Cq, the melting peak signal is strong enough for CNV detection, and the melting peaks ratio of CNV to reference is the same as in the genome and the primers were used in proportion to initial template. This approach would not seem to work if PCR were allowed to reach plateau. In an illustrative PCR reaction, in addition to primers and template, reagents may include Mg++, Tris, BSA, Taq polymerase, and dNTPs. Limiting the dNTPs and Taq polymerase concentration (Examples 2 and 4, respectively) limited amplification at a level for which CNV ratios were distinguishable when PCR was allowed to reach its plateau.

Example 2—Varying dNTPs Study

Figure 3A:
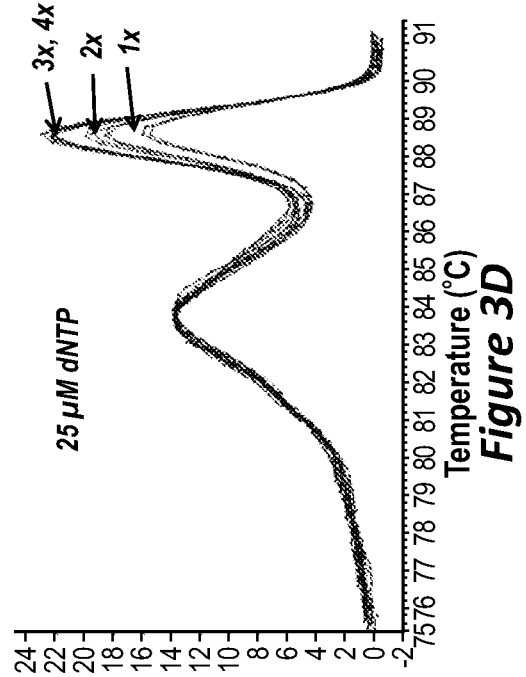
FIG. 3A illustrates melting curves of PCR at standard dNTP concentration.

From FIG. 3A one can see that at a standard 200 µM dNTP concentration, when PCR is allowed to plateau, the melting peaks of the 4 different copy samples of chromosome X are indistinguishable.

Figure 3B:
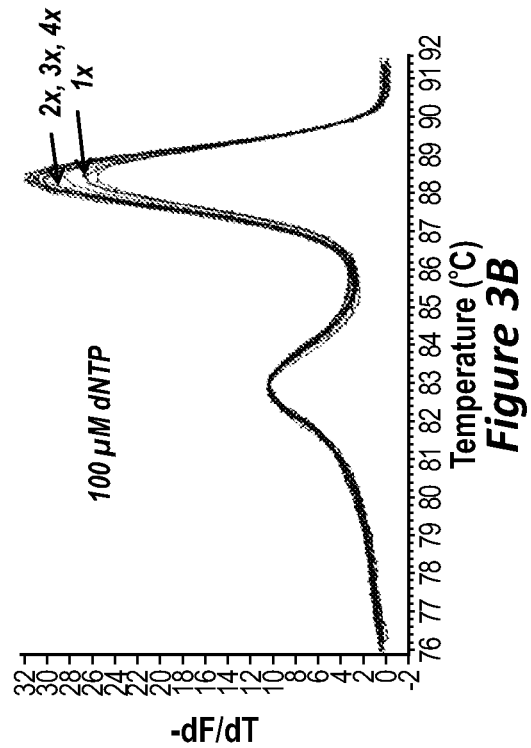
FIG. 3B illustrates melting curves of PCR at 100 μM dNTP concentration.

When dNTP concentration is decreased to 100 µM, the peaks of the 1 and 2 copy samples are slightly distinguishable. Ratios of 50% CNV (2:1) were barely distinguishable at this concentration, but the 33% and 25% CNV were not. With 100 µM dNTP concentration (FIG. 3B), at cycle 35 it is believed that primer extension begins to be limited.

Figure 3C:
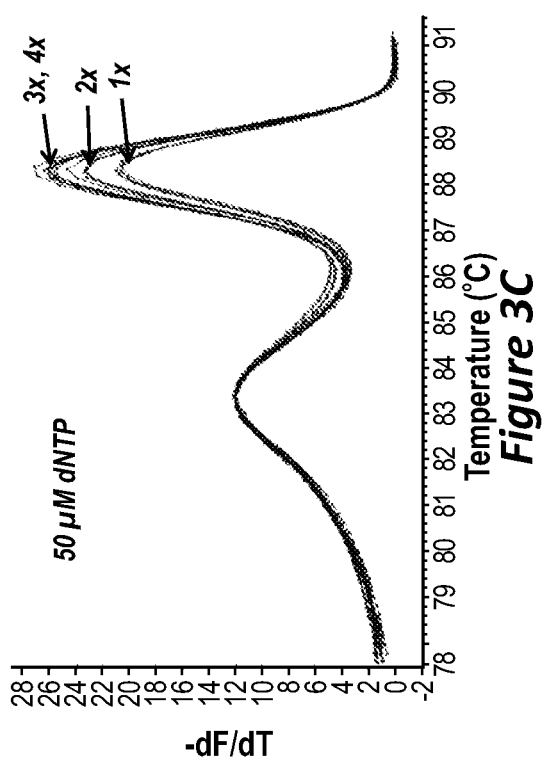
FIG. 3C illustrates melting curves of PCR at 50 μM dNTP concentration.
Figure 3D:
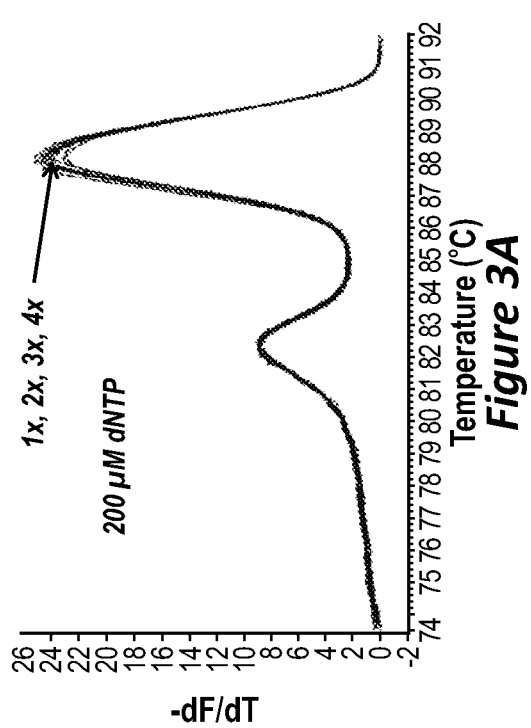
FIG. 3D illustrates melting curves of PCR at 25 μM dNTP concentration.

When dNTP concentration is decreased further to 50 µM and 25 µM (FIGS. 3C and 3D, respectively), peaks of the 1, 2 and 3 copy samples are distinguishable from each other, equivalent to the resolution obtained by stopping standard PCR a few cycles after Cq ($27^{th}$ cycle, FIG. 2C), for which the ratio of 33% different CNV were distinguishable.

Figure 3E:
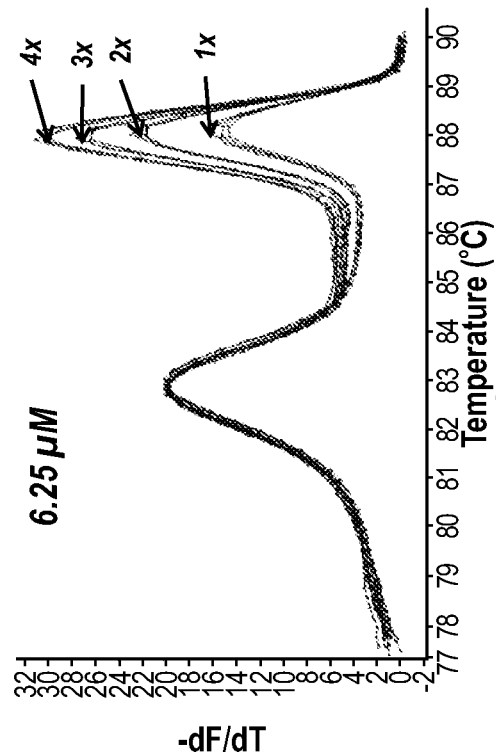
FIG. 3E illustrates melting curves of PCR at 12.5 μM dNTP concentration.
Figure 3F:
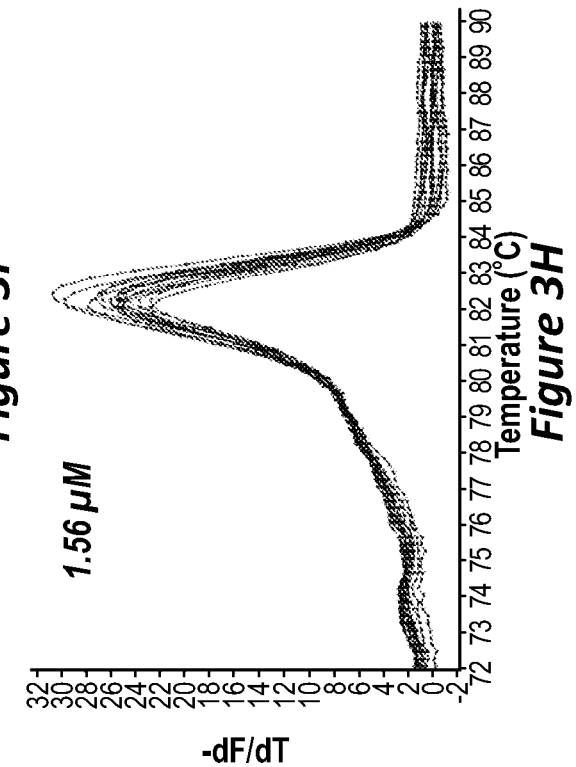
FIG. 3F illustrates melting curves of PCR at 6.25 μM dNTP concentration.
Figure 3G:
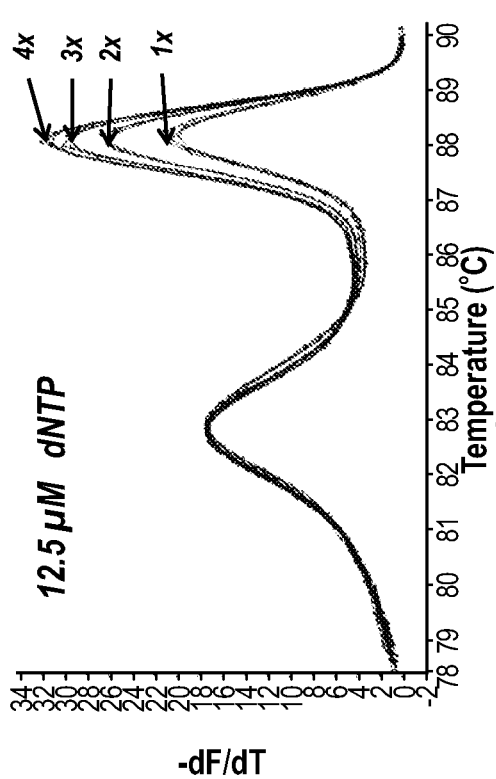
FIG. 3G illustrates melting curves of PCR at 3.125 μM dNTP concentration.

When dNTP concentration is decreased to 12.5 µM, 6.25 µM, and 3.125 µM, melting peaks corresponding to samples having 1, 2, 3, and 4 copies of chromosome X are clearly distinguishable, equivalent to the standard PCR that was stopped at Cq (cycle 24), for which ratios of 25% differences CNV (4:3) were well distinguished. For a dNTP concentration of 3.125 µM (FIG. 3G), the melting peak signal is not as strong as when dNTP concentration was 12.5 µM (FIG. 3E) or 6.25 µM (FIG. 3F), but the 1, 2, 3 and 4 copy of chromosome X melting peaks are better separated. As dNTP concentration decreased from 12.5 µM to 3.12 µM dNTP (FIG. 3G), the lower the dNTP concentration, the better separation of the CNV melting peaks. dNTP at 6.25 µM seemed the best concentration to detect CNVs in the genome.

When dNTP concentration was further decreased to 1.56 µM (FIG. 3H), only shorter reference amplicon peaks appeared but the CNV fragment on chromosome X was not present.

Figure 3H:
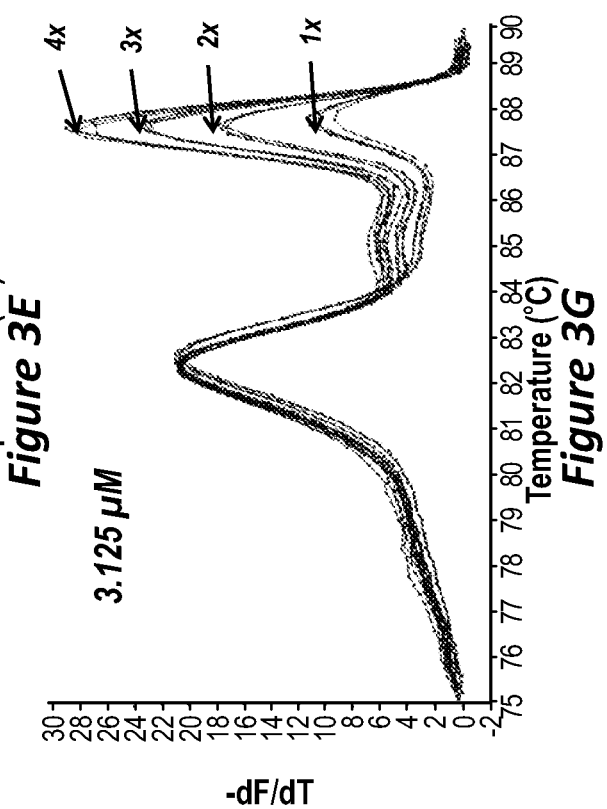
FIG. 3H illustrates melting curves of PCR at 1.56 μM dNTP concentration.

At standard dNTP concentration (200 µM) PCR, at an earlier cycle of PCR the higher Tm (or longer amplicon) melting peak has a higher amplitude melting peak, and the lower Tm (or shorter amplicon) melting peak has a lower amplitude melting peak. Both melting peaks first appear at the same cycle. This suggests that amplification efficiency of both fragments is the same. As dNTP concentrations decrease, the relative amplitude of the higher Tm peak decreases and that of the lower Tm peak increases. When the dNTP concentration reaches 1.56 µM, the lower Tm fragment was amplified, but the higher Tm fragment is not amplified at all (FIG. 3H). This suggests that as dNTP concentration decreases, amplification efficiency decreases more rapidly for the longer amplicon.

FIG. 1A illustrates duplex amplification of a fragment of CFTR exon 6 on chromosome 7 and a fragment of CYBB exon 10 with different dNTP concentrations. FIG. 1B illustrates melting curves of the duplex amplification illustrated in FIG. 1A.

As the dNTP concentration is decreased from 200 µM to 0.78 µM, the PCR Cq occurs 3 cycles later (FIG. 1A). As dNTP concentration decreases, the relative amplitude of the longer amplicon melting peak decreases while that of the shorter amplicon melting peak increases (FIG. 1B).

CNV detection by control of dNTP concentration provides better results than those obtained by control of PCR cycle number. Without being bound to theory, this may be because CNV detection by decreasing dNTP concentration maintains the ratio of target and reference products at the same level even as PCR is allowed to reach plateau. Because the dNTPs are limiting, the ratio of CNV and reference is preserved regardless of the initial template concentration even when PCR reaches plateau. Such ratio may not necessarily be maintained if limiting primer concentration, as each primer only affects its amplicon.

Example 3—Varying Template Concentration

Figures 4A, 4B:
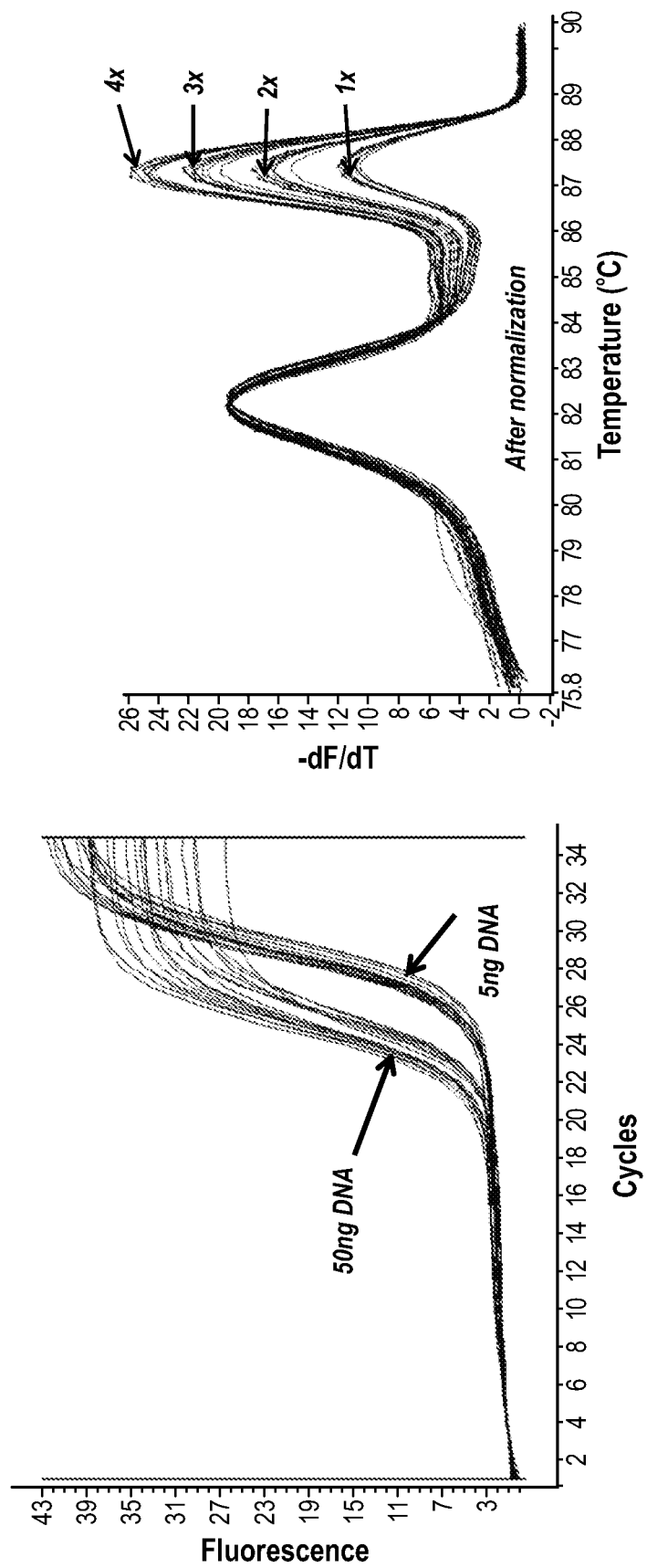
FIG. 4A illustrates PCR amplification at 10-fold different concentrations of starting samples.
FIG. 4B illustrates melting curves of the amplicons of FIG. 1A using one embodiment of the methods disclosed herein.

Next, 10-fold different concentrations (5 ng and 50 ng) of genomic DNA templates using 6.25 uM Mg++ are compared. FIG. 4A shows that the Cq of the 5 and 50 ng DNA templates are different. But once all the samples reach PCR plateau, the ratio of CNV to reference melting peaks is unaffected by the initial 10-fold template concentration difference (FIG. 4B). CNV detection by control of dNTP concentration does not need template concentration adjustment for the result to be consistent.

Example 4—Varying the Polymerase

Taq polymerase can also be used to limit PCR while keeping CNV ratios constant during PCR even while using standard dNTP concentrations (200 µM). With the standard KlenTaq1 polymerase concentration (0.04 U/µL), the melting peaks corresponding to 4 different copy numbers of chromosome X are generally indistinguishable (FIG. 5A). At 0.02 U/µL KlenTaq1, the melting peaks corresponding to samples having 2 and 3 copies of chromosome X were separated, but the separations were small (FIG. 5B). At 0.01 U/µL KlenTaq1, the melting peaks corresponding to the 1 and 2 copy samples were well separated. The melting peaks of the 2, 3, and 4 copy samples were separated, but not well (FIG. 5C). At 0.005 U/μL KlenTaq1 polymerase, only the shorter amplicon amplified (FIG. 5D). Below 0.005 U/μL KlenTaq1 polymerase, neither segment amplified sufficiently to be detected.

Example 5—Blinded Study 1: Trisomy 13, 18, and 21

Figure 6A:
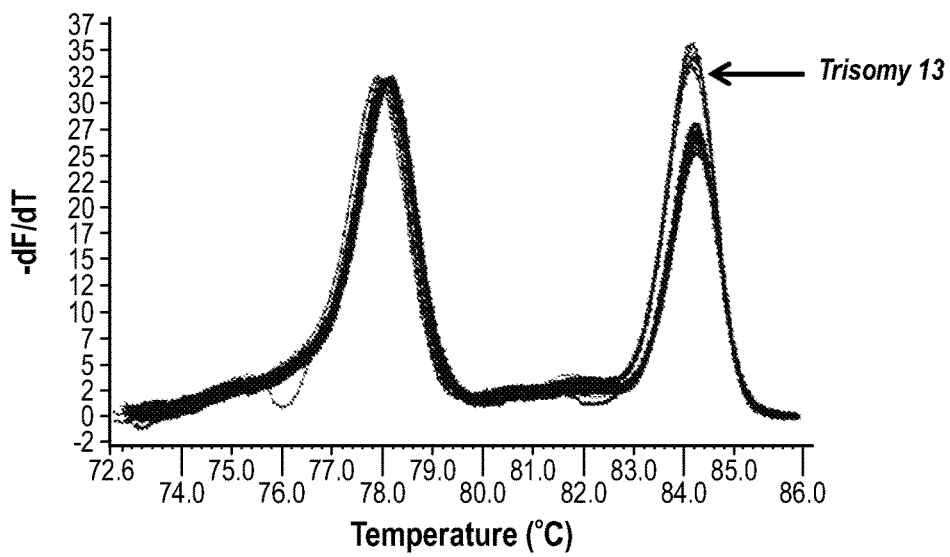
FIG. 6A illustrates a summary of a blind test of trisomy 13 samples using one embodiment of the methods disclosed herein.
Figure 6B:
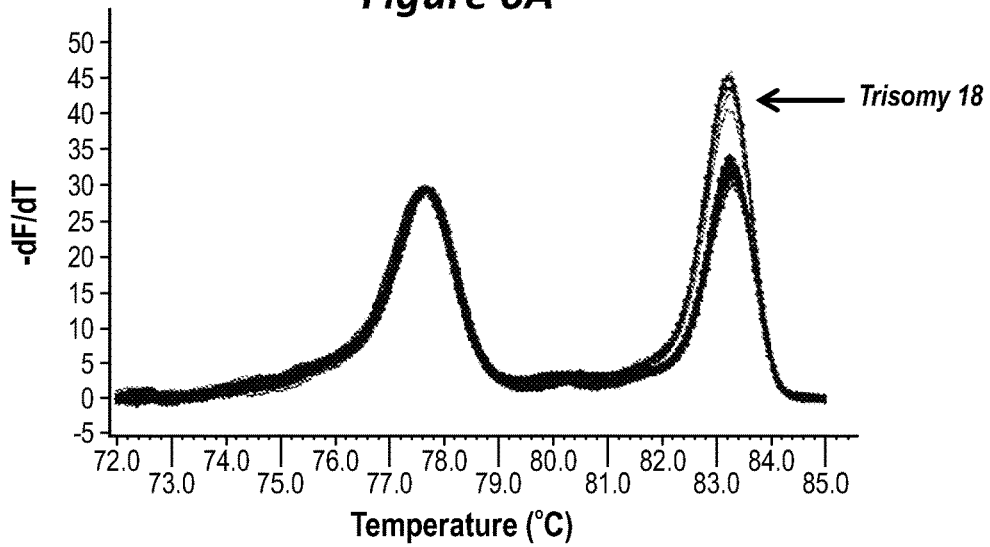
FIG. 6B illustrates a summary of a blind test of trisomy 18 samples analyzed using one embodiment of the methods disclosed herein.
Figure 6C:
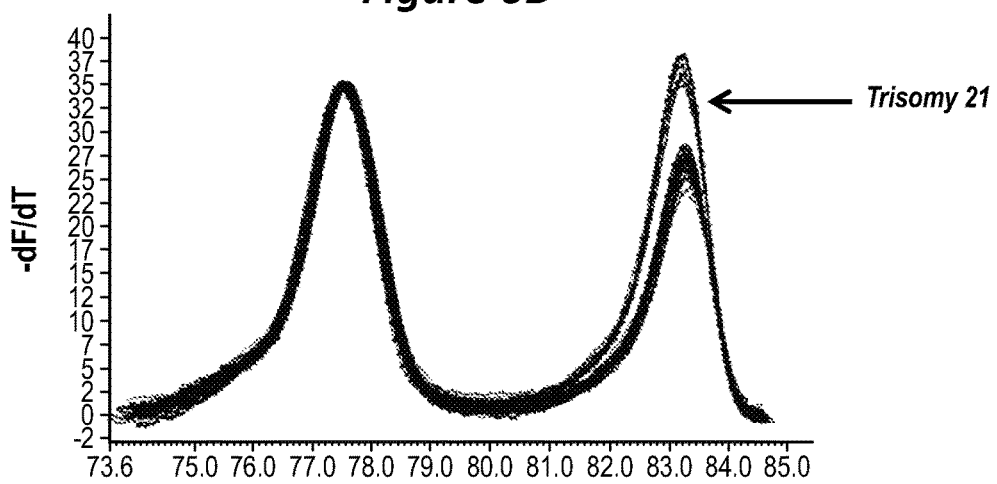
FIG. 6C illustrates a summary of a blind test of trisomy 21 samples analyzed using one embodiment of the methods disclosed herein.

Trisomies 13, 18, and 21 are the most common in humans. The CNV to reference ratio of wild-type is 1 (2:2); the CNV to reference ratio of trisomy is 1.5 (3:2) or 33% difference between the highest (trisomy) peak and the smaller reference peak. Duplex PCR with 6.25 μM dNTP concentration was used for the blinded test of trisomies 13, 18, and 21. Fifty previously typed samples included trisomy 13, 18, and 21 as well as wild-type samples with initial concentrations ranging from 10 ng/μL to 200 ng/μL were amplified. All trisomy and wild-type samples maintained their copy number ratio until the PCR plateau. The trisomy and wild-type were easily distinguishable by inspection of the CNV melting peak amplitudes, as well as systematically and automatically by unbiased hierarchical clustering. Nine of the samples were identified as trisomy 13 (FIG. 6A), 8 as trisomy 18 (FIG. 6B), 13 as trisomy 21 (FIG. 6C), and 30 as wild-type. The 2:2 copy ratio of wild-type and 3:2 copy ratio of trisomy sample melting peaks were clearly distinguishable. The CNV determination was perfectly correlated to the previously established genotypes. The blinded test sensitivity and specificity according to the automatic classification were both 100%.

The same samples were analyzed using the standard method for detecting CNV by calculating real-time PCR ΔΔCq without adjusting the template concentration [22]. The trisomies could not be distinguished from wild-type using this method. For a 2:2 genomic copy number ratio, the ΔΔCq equals 0. Wild-type and trisomy exhibit a 3:2 ratio for which the ΔΔCq is less than 1, which is difficult to detect reliably.

Example 6—Blinded Study 2, Chromosome X and Y Copy Number

The copy number ratios of chromosome 7 to chromosome X to chromosome Y of a normal male are 2:1:1; of a normal female, 2:2:0; in the chromosome cell line NA03623, 2:3:0. Normalized to one chromosome 7 copy, the ratios of chromosome 7 to chromosome X to chromosome Y of normal male is 1:0.5:0.5; normal female is 1:1:0; three copy chromosome cell line NA03623 is 1:1.5:0 (Table 2 of FIG. 7). Table 1 provides the chromosome copy numbers of samples shown in FIG. 7.

Figure 7:
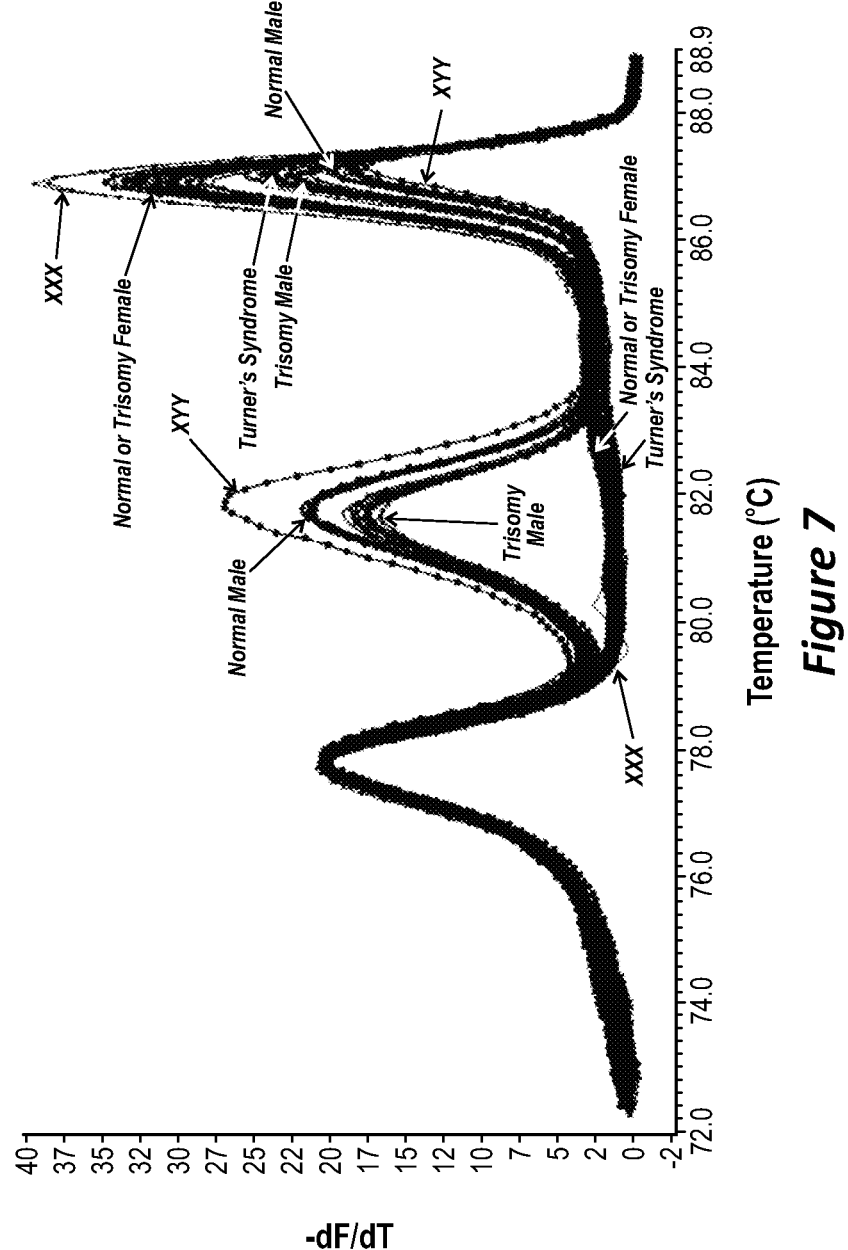
FIG. 7 illustrates a summary of a blind test of sex chromosomes analyzed using one embodiment of the methods disclosed herein.

Fifty previously typed samples with triploid sex chromosome abnormalities as well as wild-type were used for the sex chromosome CNV blinded test using triplex PCR with the standard PCR mixture except 6.25 μM dNTP. Wild-type male and female samples were easily distinguished by copy number ratios of chromosome X and Y (FIG. 7). Twenty two samples exhibited the same ratios as normal female. These could be either wild-type or triploid with 3 copy of chromosome X. 6 samples exhibited 2 copies of chromosome 7 and 1 copy of chromosome X without chromosome Y; 8 exhibited the same ratios as normal male; 11 were triploid with 2 copy of chromosome X and 1 copy of chromosome Y (FIG. 7). The CNV ratios of all samples were correctly typed except for two samples that array analysis showed 1 copy of chromosome X and no copies of chromosome Y. These two samples were re-analyzed using microarrays and found to be wild-type at the locus analyzed.

Example 7—Detecting Heterozygous Deletions

Figure 8:
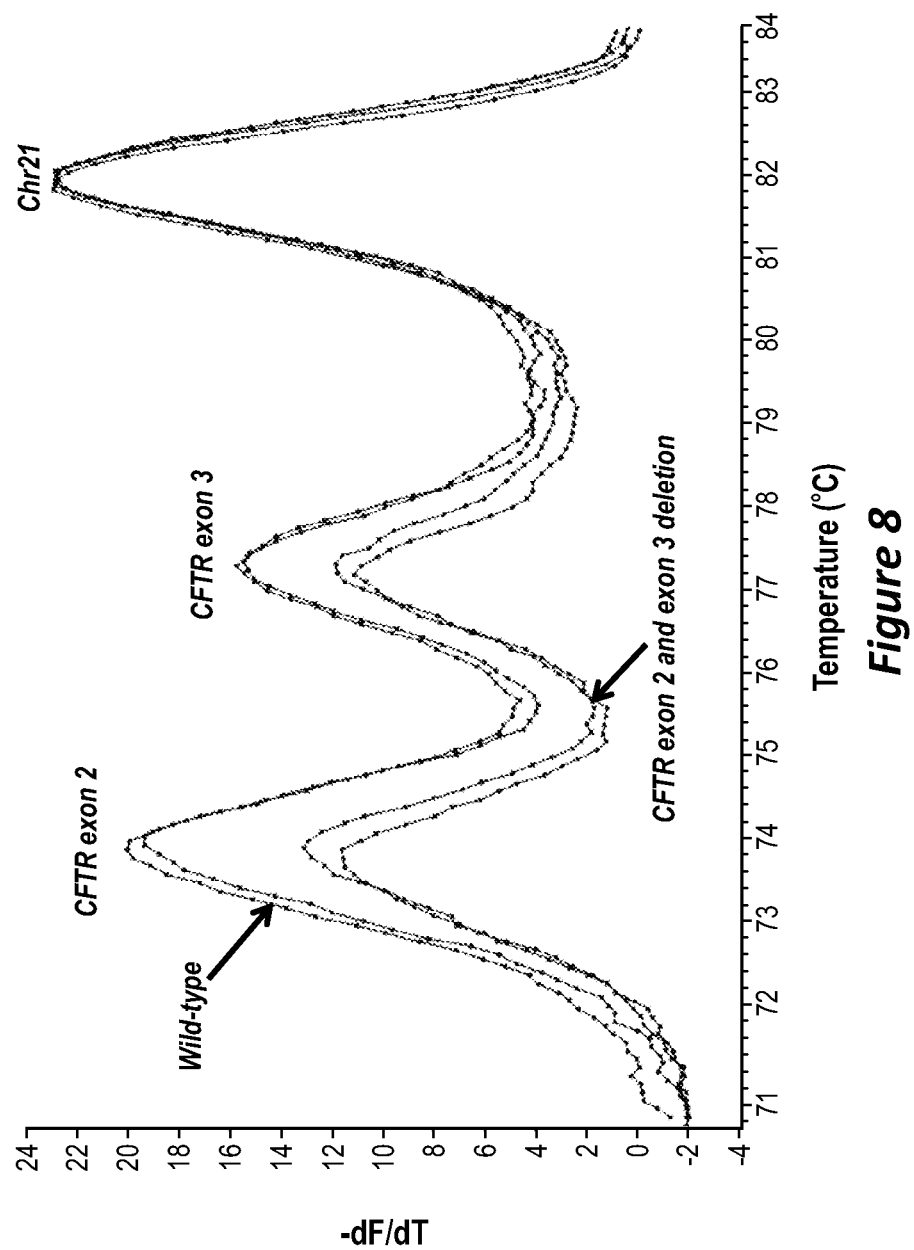
FIG. 8 illustrates analysis of heterozygous deletions using one embodiment of the methods disclosed herein.

About 1-3% genetic diseases are associated with heterozygous large deletions. These deletions could include one or multiple exons or even an entire gene. In this study, a CFTR exon 2 and exon 3 heterozygous deletion in cell line NA18668 was used as an example. Triplex PCR was used to detect CFTR exon 2 and exon 3 deletions simultaneously. Short amplicons of CFTR exon 2 and exon 3 for CNV detection were chosen to minimize the possibility of unexpected variants, e.g. SNPs that could affect amplification in experiments. In these studies, the Tms of the target amplicons CFTR exon 2 (Tm 73° C.) and exon 3 (Tm 77° C.) were lower than the Tm of the reference amplicon on chromosome 21 (Tm 83° C.). The cell line NA18668 clearly has a heterozygous deletion in CFTR exon 2 and exon 3 from copy number ratio comparison with wild-type (FIG. 8). This study also confirmed that in designing reference and target amplicons for determining copy number variation, the relative order of Tms may be arbitrary and may not affect the efficacy of the assay.

Example 8—SYBR Green Study

Figure 9:
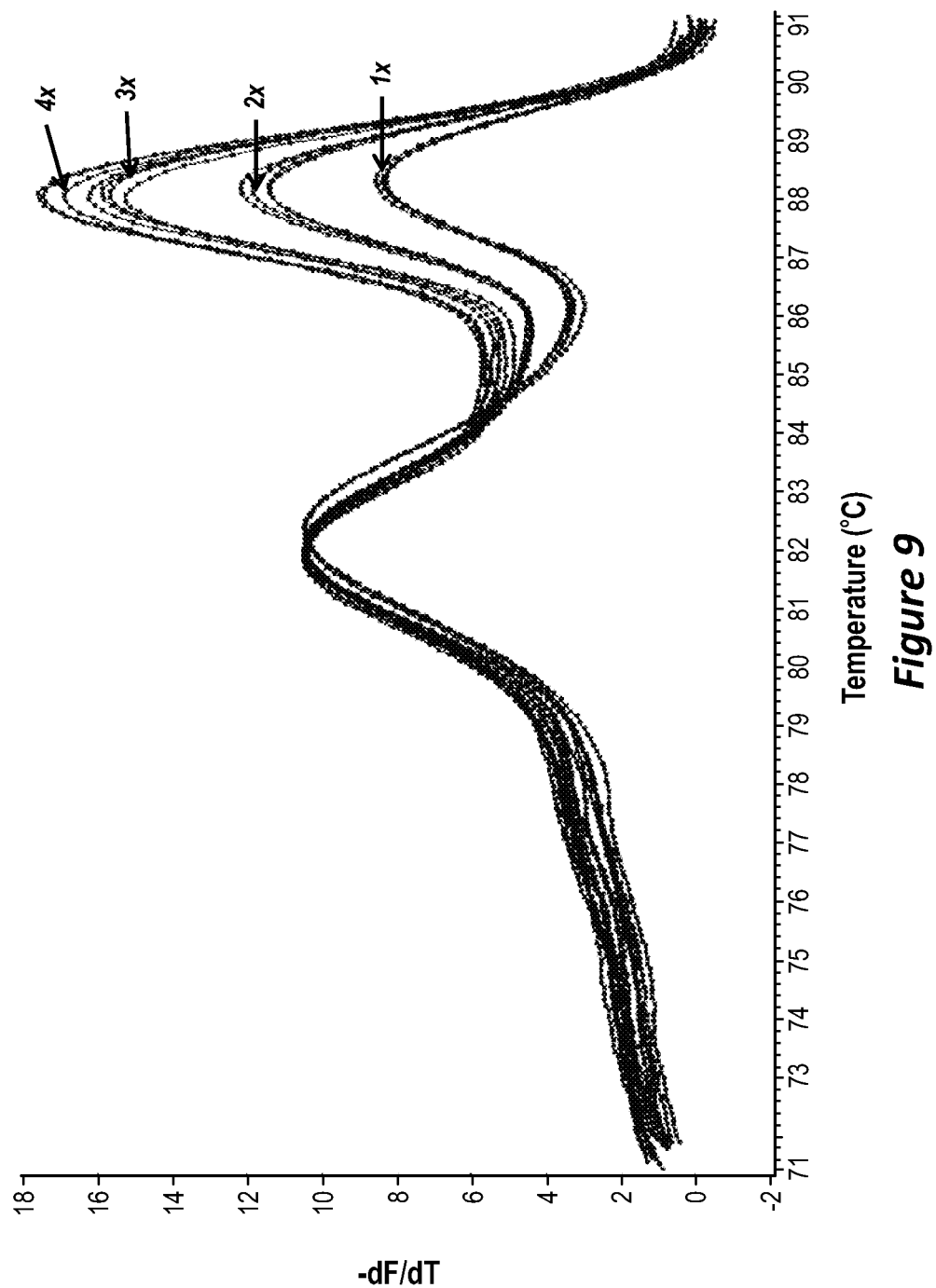
FIG. 9 illustrates analysis of copy number variations using a non-saturating dye and one embodiment of the methods disclosed herein.

SYBR Green was used instead of LCGreen Plus for CNV detection. The 1, 2, and 3 copy number samples were distinguishable from their melting peaks at dNTP concentrations of 12.5 μM (not shown) and 6.25 μM (FIG. 9).

Example 9—EGFR Study

Figure 11:
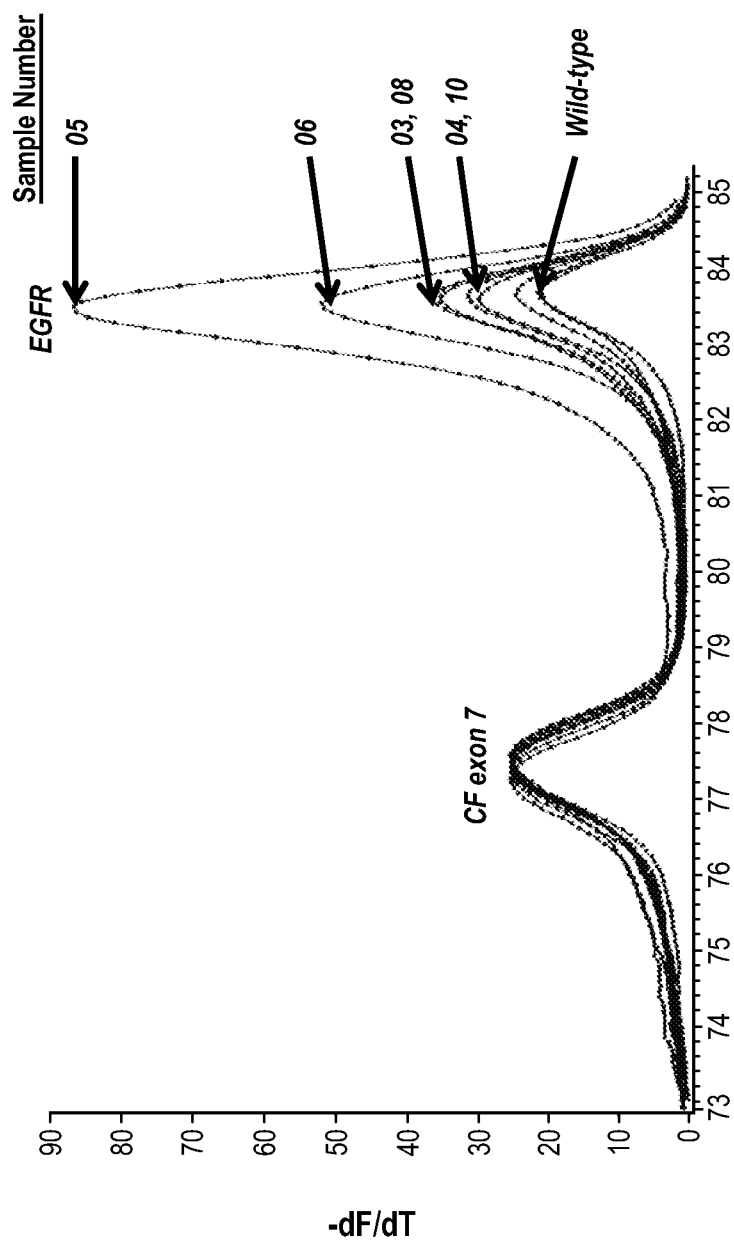
FIG. 11 illustrates analysis of copy number variations of cancer samples using one embodiment of the methods disclosed herein.

EGFR copy number changes may be an important marker for pathogenesis and targeted therapy for lung cancer. ARUP Laboratories provided DNA extracted from formalin-fixed and paraffin-embedded lung tumors from eight, de-identified patients. The amount of DNA in each sample was not measured. CFTR exon 7 was used as the reference DNA target to estimate the level of EGFR DNA (an amplicon from exon 20). Duplex PCR reactions (10 μL) contained 0.5 μM forward and reverse primer, 6.25 μM dNTP, 0.4 U KlenTaq1™ (Ab Peptides), 64 ng antiTaq antibody (eEnzyme), 2 mM Mg, 50 mM Tris (pH 8.3), 500 μg/ml bovine serum albumin, 1×LCGreen® Plus (BioFire Diagnostics) and 1 μL tumor DNA or 25 ng wild-type DNA. PCR was performed on the LightCycler 480 (Roche) with denaturation at 95° C. for 2 minutes followed by 40 cycles of 95° C. for 10 s, 65° C. for 30 s, and 72° C. for 10 s. High-resolution melting acquisition was performed at a ramp rate of 0.04° C./s from 65° C. to 95° C. with 15 acquisitions/° C. The data were analyzed using the same method as in Examples 1-8. FIG. 11 shows duplex PCR amplification of CFTR exon 7 and EGFR using 8 non-small cell lung cancer (NSCLC) samples and 1 wild-type reference. One of the NSCLC samples (#02) EGFR had the same copy number as wild-type (2 copies). Others show an increase in EGFR copies, with the EGFR copy number greater than wild-type (or more than 2 copies/cell).

Example 10—Quantification

Figure 12:
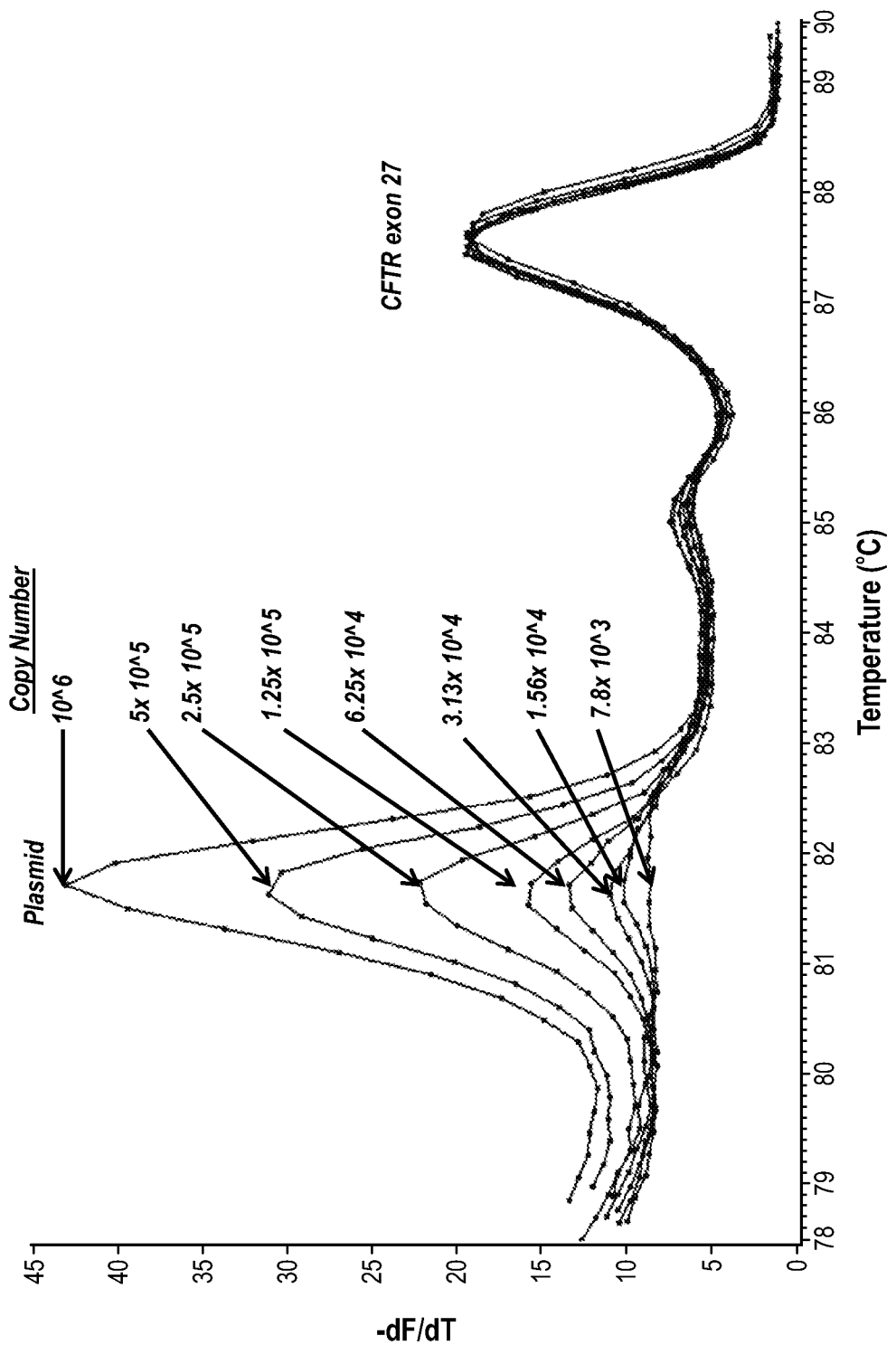
FIG. 12 illustrates the results of quantification of samples using one embodiment of the methods disclosed herein.

The methods of limiting dNTP concentration during PCR may be used for quantification. The CFTR gene, exon 27, was used as reference. The primers sequences are shown in FIG. 10. Different diluted plasmids were used as the qualification target. Serial 2-fold dilutions of the plasmid from 10^6 copies to 7.8×10^3 copies (128-fold) were made. Multiplex PCR with 6.25 µM dNTP concentration was used. As illustrated in FIG. 12, all template concentrations were distinguishable.

Example 11—Relative Gene Expression Using Two-Step PCR

Figure 13:
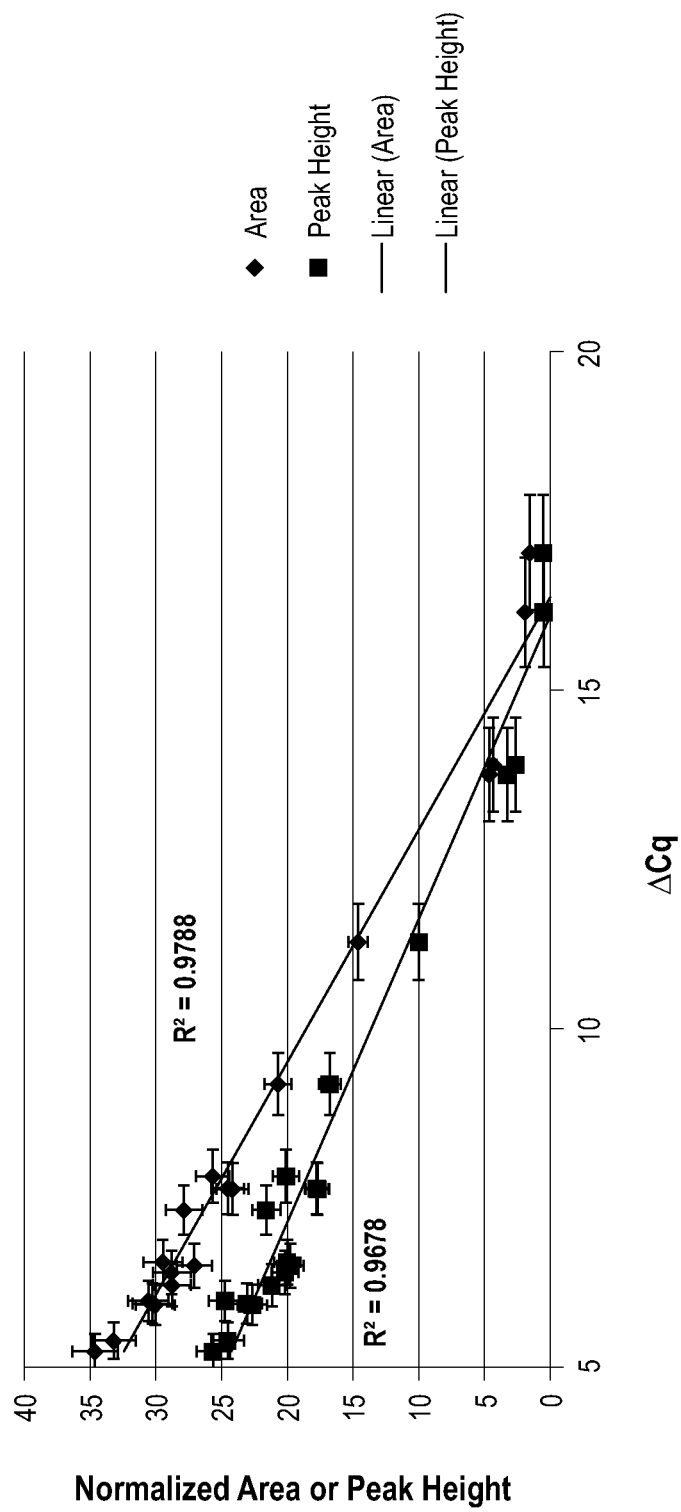
FIG. 13 illustrates the correlation of relative gene expression determined by two embodiments of the methods disclosed herein to conventional quantitative PCR.

FIG. 13 illustrates the correlation of relative gene expression determined by 1) multiplex PCR with limited dNTPs (area or peak height) and the methods of analyzing melting data disclosed herein, and 2) conventional quantitative PCR ($\Delta$Cq). The expression of the mouse Oasl2 gene was measured in several mouse cell lines treated with different combinations of Borelia Burgdorferi and Poly I/C (polyinosinic-polycytidylic acid). The primer sequence and PCR amplicon size of beta-actin and Oasl2 are shown in FIG. 10. Studies with the mouse cell lines B6, CBCb1, C3H, C3H/HeN, IFNARO/BL6 and IFNARO/C3H, were performed in triplicate. mRNA was extracted using the Mouse RIBOPURE™-Blood RNA Isolation Kit and the RNAs were reverse transcribed using SUPERSCRIPT® II (Life Technologies). Relative Oasl2 gene expression was measured by 2 methods. In the first, qPCR was performed and the $\Delta$Cq between beta-actin and Oasl2 determined after amplifying 20-50 ng of cDNA. In the second, the same cDNA was used in limited dNTP multiplex PCR (using beta-actin as the reference) followed by melting. The PCR reagents and protocol were the same as for Example 9. The melting peak heights and area of Oasl2 were measured and normalized to those of the beta-actin control.

The correlation between $\Delta$Cq by qPCR and multiplex PCR with limiting dNTPs, using either melting peak height or peak area is high ($R^2$=0.9788 and $R^2$=0.9678). The standard deviation between triplicates is less using limiting dNTPs as compared to $\Delta$Cq and only one PCR reaction is needed compared to 2 reactions.

Example 12—Relative Gene Expression Using One-Step Reverse Transcription PCR

Figure 14:
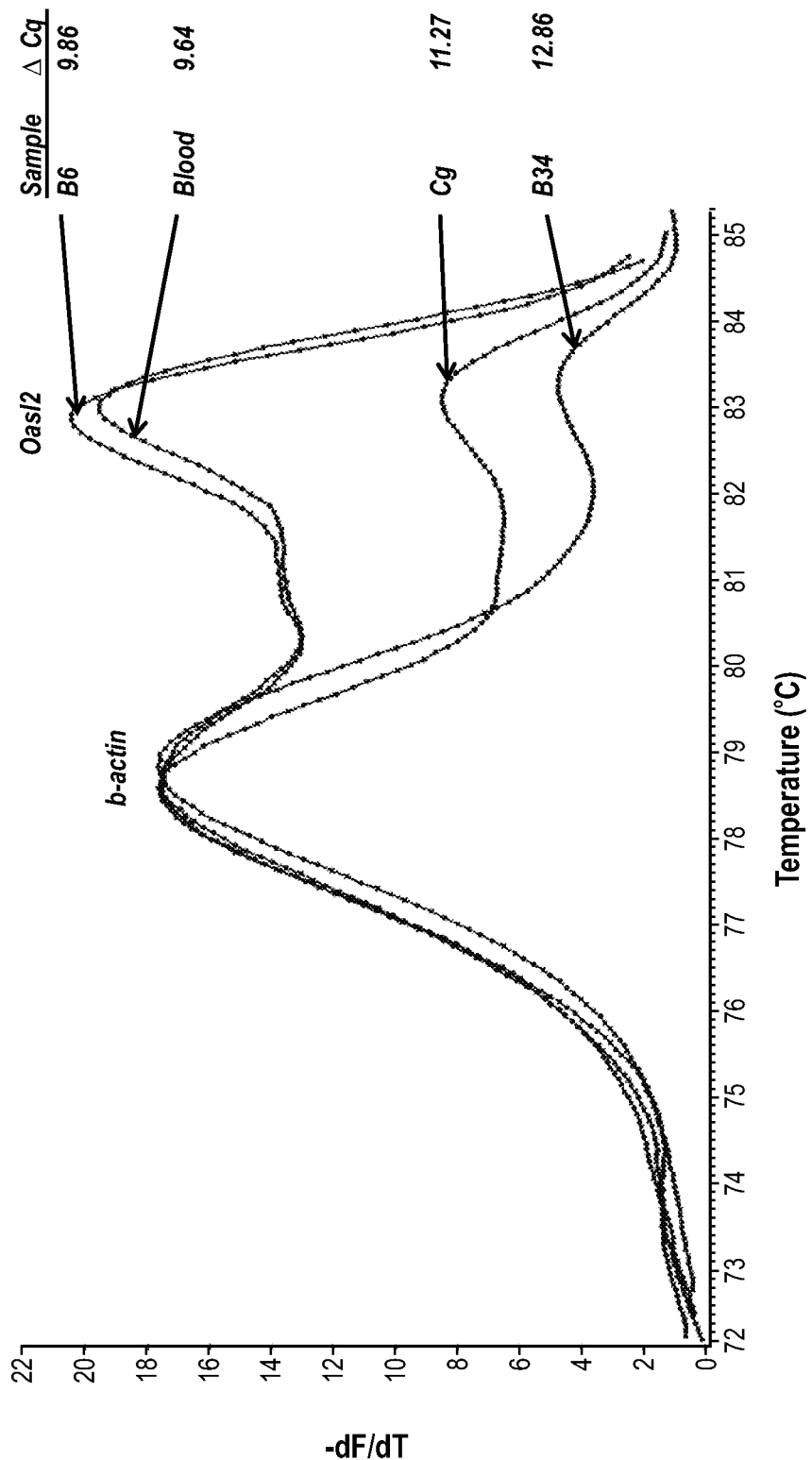
FIG. 14 illustrates analysis of relative gene expression using one embodiment of the methods disclosed herein.

FIG. 14 illustrates the derivative melting curves of duplex one-step reverse transcription PCR with limited dNTPs at a concentration of 6.25 µM for four mouse RNA samples. Beta-actin was used as the reference gene and OasI2 was the target. Three mouse cell lines (B6, B34 and Cg) were exposed to Borelia Burgdorferi. RNA from mouse blood and the three cell lines were extracted using the Mouse RiboPure™-Blood RNA Isolation Kit (Life Technologies). One step RT-PCR was performed in 20 µL of 50 µM dNTPs, 3 mM $MgCl_2$, 500 µg/ml bovine serum albumin, 0.5× LCGreen® Plus (BioFire Diagnostics), 0.5 µM of each primer, 0.4 U KlenTaq1™ (Ab Petides), 64 ng anti-Taq antibody (eEnzyme), 0.6 U Transcriptor reverse transcriptase (Roche) and 50 to 200 ng of purified RNA. The RT-PCR was performed on the LightCycler 480 (Roche) as follows: reverse transcription at 42° C. for 15 min, initial denaturation at 95° C. for 15 sec, then 40 cycles of 95° C. for 10 sec and 62° C. for 30 sec. Immediately following PCR a melting curve was generated and analyzed as previously described. For comparison, $\Delta$Cqs were obtained by qPCR performed with cDNA obtained using the SuperScript® II reverse transcription kit. The $\Delta$Cq and melting peak height correlated well. The peak heights of OasI2 are different reflecting different OasI2 gene expression relative to beta-actin in the 4 mouse samples.

The OasI2 gene expression level of mouse blood and cell B6 are the same in $\Delta$Cq and melting peak height while cell B34 and Cg expressed less OasI2 (FIG. 14). This one step PCR was also compared to the results obtained by 2-step PCR of beta-actin and OasI2 using random hexamers for reverse transcription as the first step with the standard dNTP concentration of 200 µM, followed by qPCR for the second step with a dNTP concentration of 6.25 µM. Results between the techniques correlated well.

Example 13—Standard Curves for Dilution Series

Figure 15A:
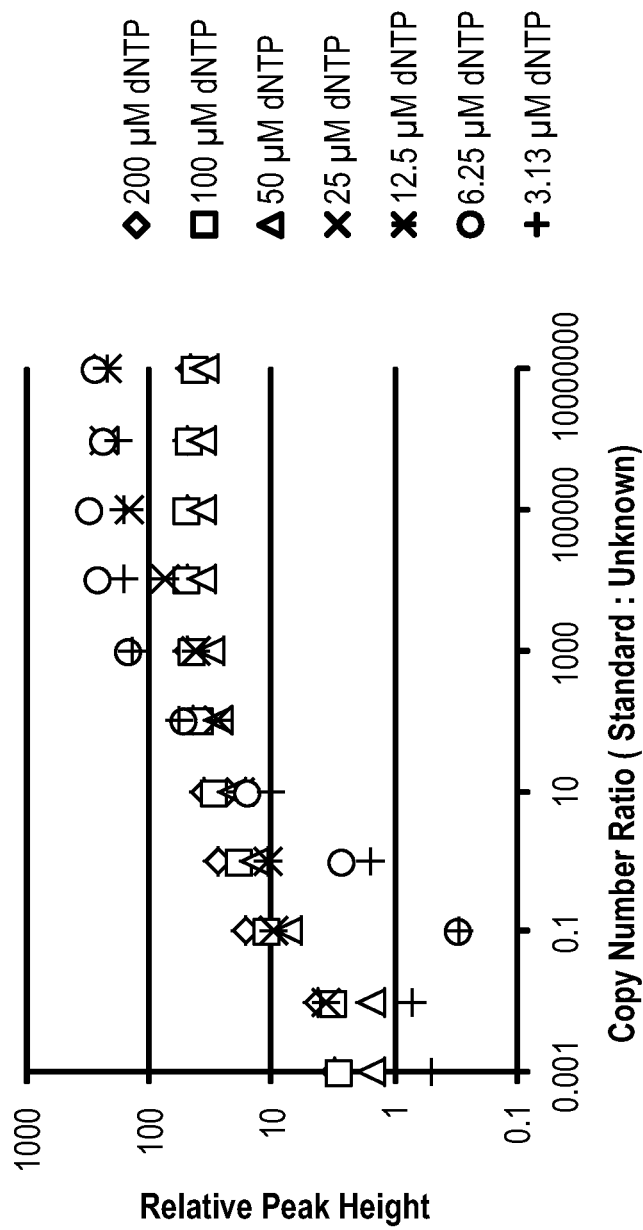
FIG. 15A illustrates a dilution series of plasmid DNA ($10^{11}$ to $10^1$) amplified with $10^4$ copies human genomic DNA with different concentrations of dNTPs.
Figure 15B:
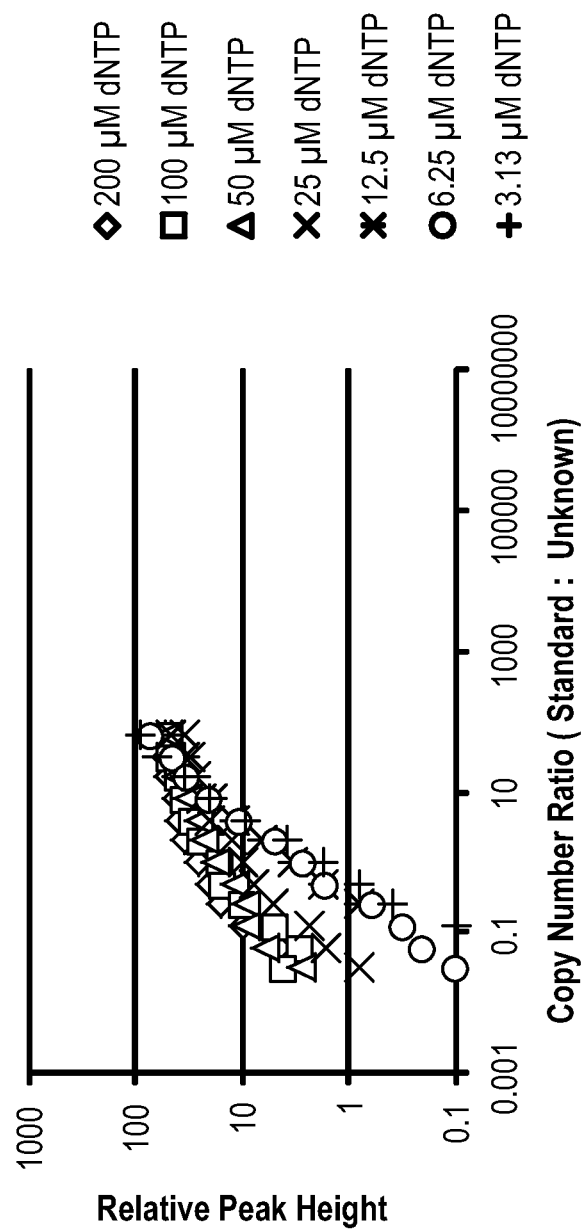
FIG. 15B is similar to FIG. 15A, except showing a 2× dilution series ($2^{20}$ to $2^9$) and mixed with $2^{14}$ copies human genomic DNA.

FIG. 15A illustrates standard curves generated from a dilution series using plasmid DNA, with $10^{11}$ to $10^1$ copies, amplified together with $10^4$ copies human genomic DNA, using different concentrations of dNTPs. The ratio between the human and plasmid DNA concentrations was plotted against the relative peak height between the human and plasmid DNA. The best separation between copy numbers was seen with 6.25 µM dNTPs, although all dNTP concentrations showed some separation between ratios of 0.1 and 1000. To explore this range further, a two-fold dilution series of the same plasmid was used between $2^{20}$ and $2^9$, and mixed with $2^{14}$ copies human genomic DNA. As seen in FIG. 15B, 6.25 µM dNTPs showed a near linear relationship, with 3.13 µM and 12.5 µM showing similar results, indicating that a standard curve can be used to determine high copy numbers.

Figure 16A:
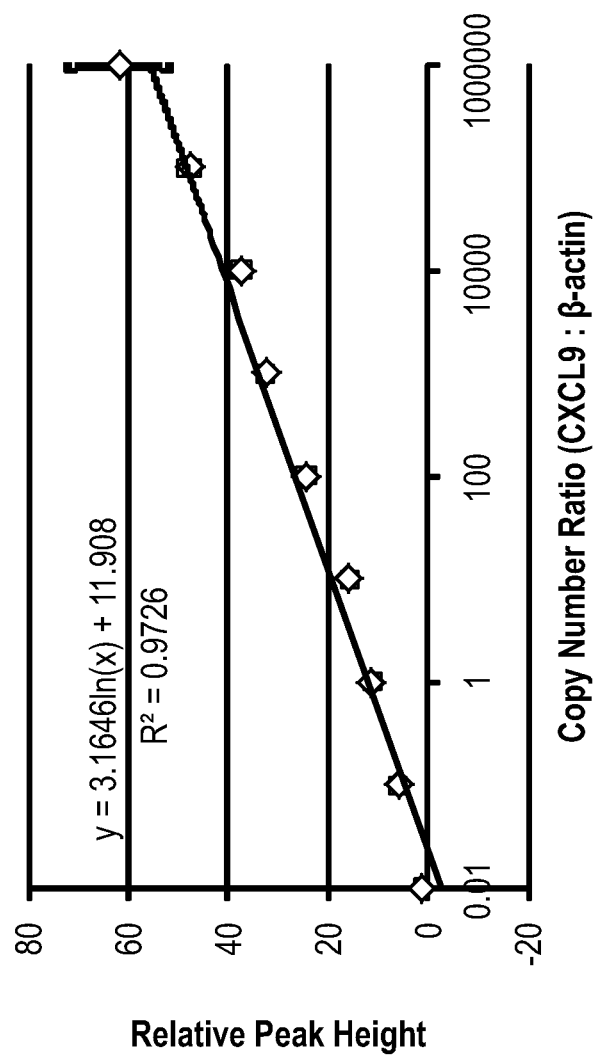
FIG. 16A is a plot of relative peak height versus copy number ratio, wherein the CXCL9 amplicon was provided at $10^{11}$ to $10^1$ copies, and amplified with $10^4$ copies of mouse b-actin cDNA as the reference gene. 25 μM dNTPs were used for each reaction.
Figure 16B:
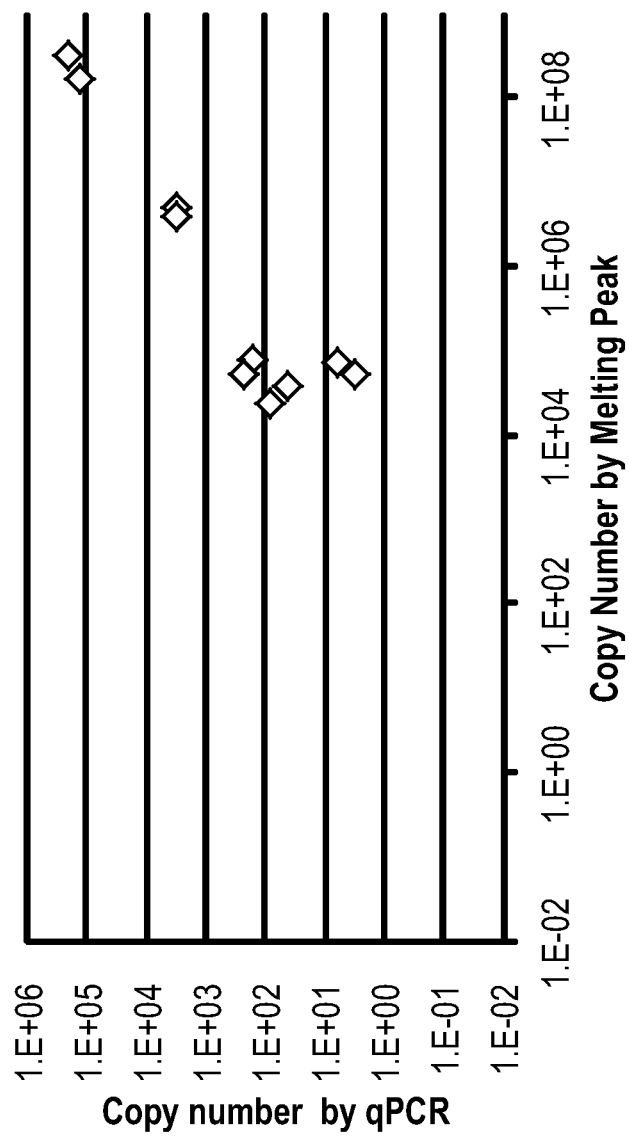
FIG. 16B illustrates the correlation between copy number as determined by a qPCR method and by relative peak height. In the qPCR method, the mouse cDNA beta-actin reference gene and target gene CXCL9 are amplified separately by qPCR. The Cq of beta-actin and CXCL9 were used to calculate the copy number of CXCL9. The CXCL9 copy number by melting peak is calculated according to the formula of FIG. 16A.

FIG. 16A is a plot of relative peak height versus copy number ratio, wherein CXCL9 amplicon was provided at $10^{11}$ to $10^1$ copies, and amplified with $10^4$ copies of mouse b-actin cDNA as the reference gene. 25 µM dNTPs were used for each reaction. A good correlation between copy number and peak height can be seen. Thus, it is understood that the methods of this disclosure may be used to determine either relative copy number or actual copy number. FIG. 16B illustrates the linear correlation between copy number as determined by a qPCR method and as determined by the methods of this disclosure. In the qPCR method, the CXCL9 target gene was amplified separately from the mouse reference gene. In the peak height method, the CXCL9 target was amplified with $10^4$ copies of the mouse b-actin cDNA reference gene and with 25 µM dNTPs. Good correlation is seen with copy numbers from 0.1 to 100,000, suggesting the relative peak height determination may have a large dynamic range.

Example 14—Single Allele Amplification with Copy Number Variation Determination

Spinal muscular atrophy (SMA) is a common recessive genetic disease. Most cases are caused by homozygous deletion of the gene SMN1. A very closely related gene, SMN2, differs from SMN1 in only a single base in exon 7 (c.840C>T). Amplification with primers common to both SMN1 and SMN2 has been used to establish the SMN1 homozygous deletion characteristic of SMA [30]. Furthermore, the various proportions of SMN1 and SMN2 produce a complicated pattern of heteroduplexes that can be matched to the copy numbers of each gene that characterize the genotype. In normal individuals, the SMN1 copy number can vary from 1 to 4 and the SMN2 copy number can vary from 0-6. However, one disadvantage of this method is that constant ratios cannot be differentiated. For example, SMN1:SMN2 copies of 1:1, 2:2, and 3:3 all give the same ratio (1:1) and the same melting curves.

In order to obtain absolute as well as relative copy numbers of SNM1 and SMN2, allele-specific PCR was performed, using one common primer and two ARMS allele-specific primers whose 3'-ends match either c.840C or c.840T. Two reactions are performed on each sample. Each reaction is multiplexed with the same reference gene and low dNTP concentrations force an early plateau before primer limitation is reached. In this example, the copy number ratio of SNM1 to the reference gene and the copy number of SNM2 to the reference gene are determined in separate reactions, although it is understood that they could be determined in the same reaction, illustratively by using a different non-ARMS primer for each allele, to result in different melting peaks for each allele. Together they establish the absolute and relative copy numbers of SNM1 and SMN2. For allele specific PCR of this example, the dNTP concentrations were reduced to 6.25 mM each and the primer concentrations were 0.5 uM each.

The primer sequences for the CFTR reference gene were:
CFTRexon6F: TTGTGATTACCTCAGAAATGATTGA (SEQ ID NO:1), and
CFTRexon6R: CATTGCTTCTTCCCAGCAGT (SEQ ID NO:2), producing an amplicon of 50 bp that melts at 78.5° C.

SMN1 and SMN2 were amplified with the same forward primer:
SMAF: TTCCTTTATTTTCCTTACAGGGTTT (SEQ ID NO:27), and 2 ARMS allele-specific primers:
SMA1R: CCTTCCTTCGATTTTGTCTG (SEQ ID NO:28), and
SMA2R: CCTTCCTTCGATTTTGTCTA (SEQ ID NO:29), producing a 48 bp product that melts at 74.5° C. for SMN1 and 73.7° C. for SNM2.

Figure 17A:
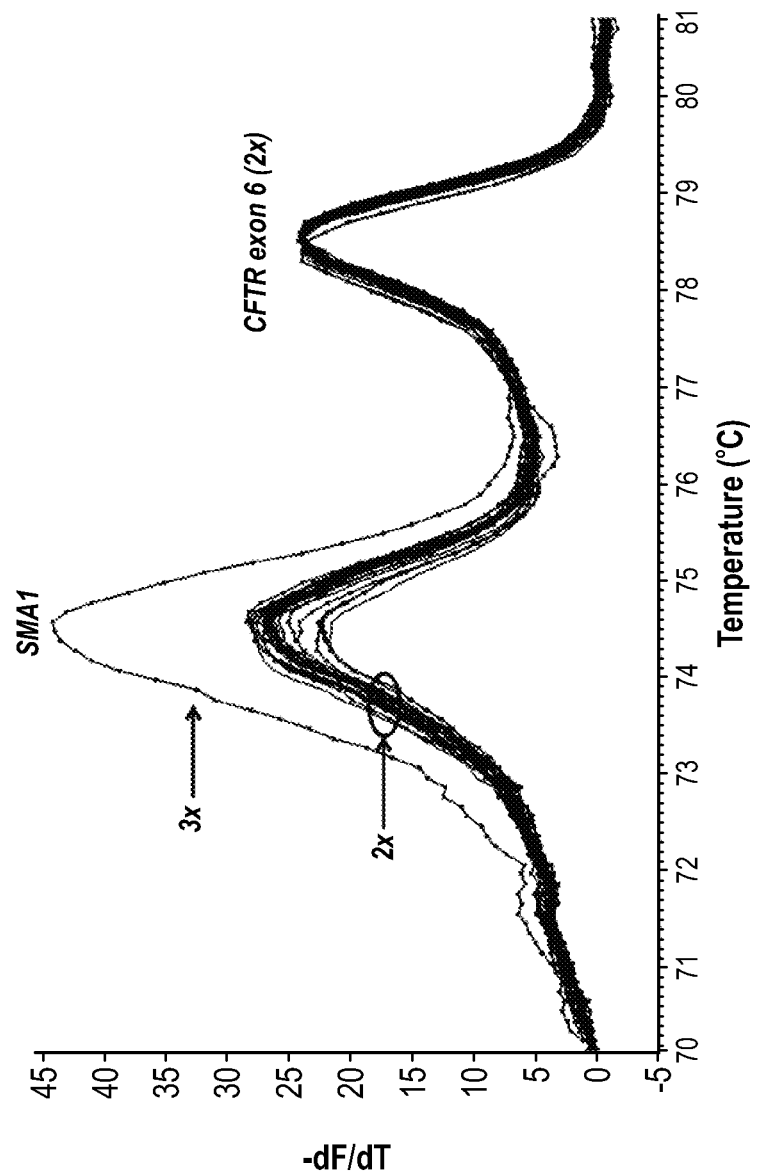
FIG. 17A shows single allele amplification to determine copy number of the SMA1 gene.
Figure 17B:
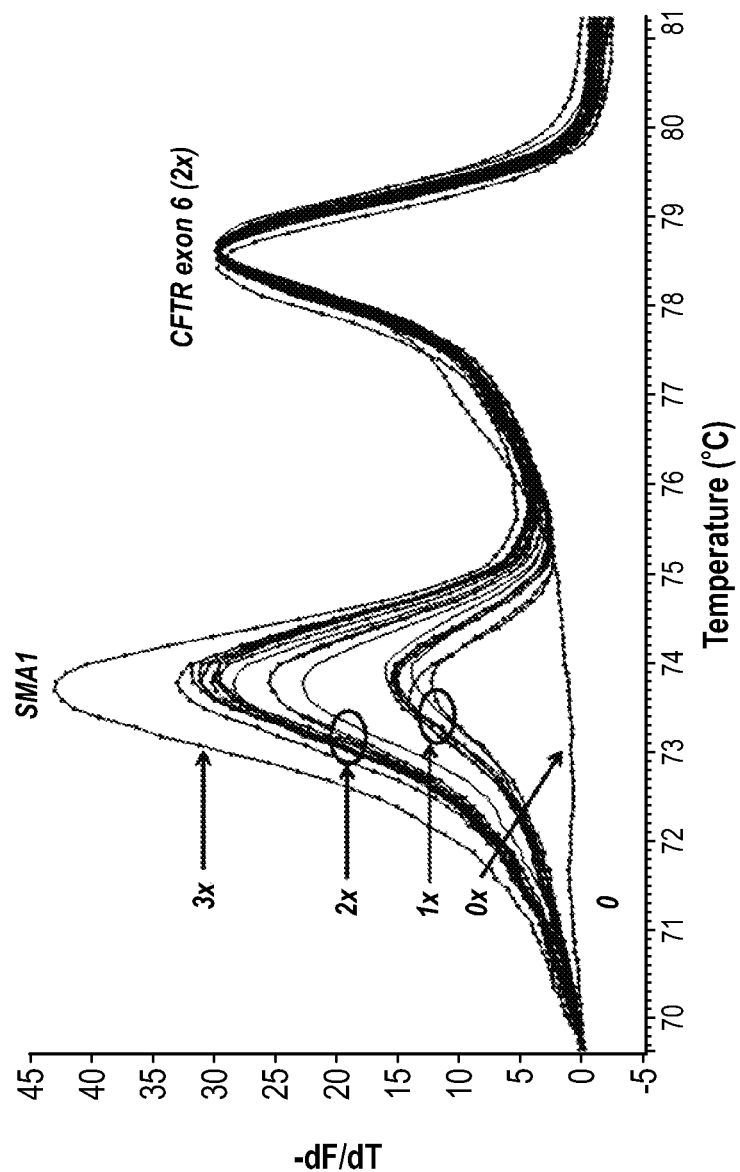
FIG. 17B is similar to FIG. 17A, but showing single allele amplification to determine copy number of the SMA2 gene.

Amplification was performed on a LC480 real time PCR instrument (Roche) with an initial denaturation of 95° C. for 2 min, followed by 32 cycles of 95° C. for 10 sec and 65° C. for 20 sec with a ramp rate of 2.2° C./s. The melting ramp occurred from 60° C. to 90° C. with 10 acquisitions per ° C. (Ramp rate 0.06° C./s). Results are shown in FIG. 17A, showing that most samples have 2 copies of SMN1, and FIG. 17B showing samples with 0, 1, 2, and 3 copies of SMN2.

Allele specific PCR combined with dNTP restriction of the PCR plateau has many uses in genotyping and allele fraction estimation. For example, a similar allele-specific PCR could be performed on a sample of hepatitis C or HIV cDNA reverse transcribed from a patient, to determine the percentage of different genotypes or variants that affect the prognosis of different therapies. Escape from therapy is a common problem of patients treated with pharmaceuticals and is evidenced by expansion of resistant clones that can be accurately measured by allele-specific PCR and dNTP restriction.

It is understood that the materials needed for any of the methods described herein may be provided as kits, including any or all of the following:

a polymerase or other enzyme suitable for the amplification method, dNTPs, illustratively in an amount below a Standard PCR Protocol Concentration, illustratively, 50 μM or less, including concentrations about 25 μM, 12.5 μM, 6.25 μM, or 3.125 μM, or any concentration in between, primers configured to amplify the locus of the target nucleic acid, primers configured to amplify the reference nucleic acid, such primers may be provided in the same or different tube as the primers configured to amplify the locus of the target nucleic acid, and protocols for performing amplification and to determine CNV of the target nucleic acid.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

REFERENCES

The contents of each of the References below, in its entirety, are incorporated herein by reference.

1. Stankiewicz P, Lupski J R (2010) Structural variation in the human genome and its role in disease. Annu Rev Med 61: 437-455.
2. Schneider M, Hirt C, Casaulta C, Barben J, Spinas R, et al. (2007) Large deletions in the CFTR gene: clinics and genetics in Swiss patients with CF. Clin Genet 72: 30-38.
3. Quemener S, Chen J M, Chuzhanova N, Benech C, Casals T, et al. (2010) Complete ascertainment of intragenic copy number mutations (CNMs) in the CFTR gene and its implications for CNM formation at other autosomal loci. Hum Mutat 31: 421-428.
4. Hartmann C, John A L, Klaes R, Hofmann W, Bielen R, et al. (2004) Large BRCA1 gene deletions are found in 3% of German high-risk breast cancer families. Hum Mutat 24: 534.
5. Agata S, Dalla Palma M, Callegaro M, Scaini M C, Menin C, et al. (2005) Large genomic deletions inactivate the BRCA2 gene in breast cancer families. J Med Genet 42: e64.
6. Petrij-Bosch A, Peelen T, van Vliet M, van Eijk R, Olmer R, et al. (1997) BRCA1 genomic deletions are major founder mutations in Dutch breast cancer patients. Nat Genet 17: 341-345.
7. Gonzalez E, Kulkarni H, Bolivar H, Mangano A, Sanchez R, et al. (2005) The influence of CCL3L1 gene-containing segmental duplications on HIV-1/AIDS susceptibility. Science 307: 1434-1440.
8. Huik K, Sadam M, Karki T, Avi R, Krispin T, et al. (2010) CCL3L1 copy number is a strong genetic determinant of HIV seropositivity in Caucasian intravenous drug users. J Infect Dis 201: 730-739.
9. Cunningham D, Humblet Y, Siena S, Khayat D, Bleiberg H, et al. (2004) Cetuximab monotherapy and cetuximab plus irinotecan in irinotecan-refractory metastatic colorectal cancer. N Engl J Med 351: 337-345.
10. Hirsch F R, Varella-Garcia M, Cappuzzo F, McCoy J, Bemis L, et al. (2007) Combination of EGFR gene copy number and protein expression predicts outcome for advanced non-small-cell lung cancer patients treated with gefitinib. Ann Oncol 18: 752-760.
11. Algars A, Lintunen M, Carpen O, Ristamaki R, Sundstrom J (2011) EGFR gene copy number assessment from areas with highest EGFR expression predicts response to anti-EGFR therapy in colorectal cancer. Br J Cancer 105: 255-262.

12. Dahabreh I J, Linardou H, Kosmidis P, Bafaloukos D, Murray S (2011) EGFR gene copy number as a predictive biomarker for patients receiving tyrosine kinase inhibitor treatment: a systematic review and meta-analysis in non-small-cell lung cancer. Ann Oncol 22: 545-552.
13. Visakorpi T, Hyytinen E, Kallioniemi A, Isola J, Kallioniemi O P (1994) Sensitive detection of chromosome copy number aberrations in prostate cancer by fluorescence in situ hybridization. Am J Pathol 145: 624-630.
14. Wang F, Fu S, Shao Q, Zhou Y B, Zhang X, et al. (2013) High EGFR copy number predicts benefits from tyrosine kinase inhibitor treatment for non-small cell lung cancer patients with wild-type EGFR. J Transl Med 11: 90.
15. International Human Genome Sequencing C (2004) Finishing the euchromatic sequence of the human genome. Nature 431: 931-945.
16. Sharp A J, Locke D P, McGrath S D, Cheng Z, Bailey J A, et al. (2005) Segmental duplications and copy-number variation in the human genome. Am J Hum Genet 77: 78-88.
17. Urban A E, Korbel J O, Selzer R, Richmond T, Hacker A, et al. (2006) High-resolution mapping of DNA copy alterations in human chromosome 22 using high-density tiling oligonucleotide arrays. Proc Natl Acad Sci USA 103: 4534-4539.
18. Komura D, Shen F, Ishikawa S, Fitch K R, Chen W, et al. (2006) Genome-wide detection of human copy number variations using high-density DNA oligonucleotide arrays. Genome Res 16: 1575-1584.
19. Lai W R, Johnson M D, Kucherlapati R, Park P J (2005) Comparative analysis of algorithms for identifying amplifications and deletions in array CGH data. Bioinformatics 21: 3763-3770.
20. Xi R, Hadjipanayis A G, Luquette U, Kim T M, Lee E, et al. (2011) Copy number variation detection in whole-genome sequencing data using the Bayesian information criterion. Proc Natl Acad Sci USA 108: E1128-1136.
21. Sepulveda N, Campino S G, Assefa S A, Sutherland C J, Pain A, et al. (2013) A Poisson hierarchical modelling approach to detecting copy number variation in sequence coverage data. BMC Genomics 14: 128.
22. D'Haene B, Vandesompele J, Hellemans J (2010) Accurate and objective copy number profiling using real-time quantitative PCR. Methods 50: 262-270.
23. Ingham D J, Beer S, Money S, Hansen G (2001) Quantitative real-time PCR assay for determining transgene copy number in transformed plants. Biotechniques 31: 132-134, 136-140.
24. Janssen B, Hartmann C, Scholz V, Jauch A, Zschocke J (2005) MLPA analysis for the detection of deletions, duplications and complex rearrangements in the dystrophin gene: potential and pitfalls. Neurogenetics 6: 29-35.
25. Schouten J P, McElgunn C J, Waaijer R, Zwijnenburg D, Diepvens F, et al. (2002) Relative quantification of 40 nucleic acid sequences by multiplex ligation-dependent probe amplification. Nucleic Acids Res 30: e57.
26. Paxton C N, Brothman A R, Geiersbach K B (2013) Rapid aneusomy detection in products of conception using the KaryoLite BACs-on-Beads assay. Prenat Diagn 33: 25-31.
27. Palais R, Wittwer C T (2009) Mathematical algorithms for high-resolution DNA melting analysis. Methods Enzymol 454: 323-343.
28. Press W H, Teukolsky S A, Vetterling W T, Flannery B P (2007) The Art of Scientific Computing: Cambridge University Press.
29. George A M, Oei P, Winship I (2003) False-positive diagnosis of trisomy 21 using fluorescence in situ hybridisation (FISH) on uncultured amniotic fluid cells. Prenat Diagn 23: 302-305.
30. Dobrowolski S F, Pham H T, Downes F P, Prior T W, Naylor E W, Swoboda K J. Newborn screening for spinal muscular atrophy by calibrated short-amplicon melt profiling. Clin Chem. 2012 June; 58(6):1033-9.

The invention claimed is:

1. A method of determining copy number variation (CNV) in a nucleic acid sample regardless of initial template concentration, the method comprising:
amplifying at least two regions of the nucleic acid sample simultaneously in the same reaction under reduced concentrations of one or more deoxyribonucleotide triphosphates (dNTPs) such that amplification is limited by exhaustion of dNTPs without limiting primer concentration, thereby driving the reaction into plateau while preserving an initial ratio of the at least two regions;
generating a melting curve of the amplicons generated in the amplifying step; and
comparing the melting curve to a melting curve generated from an amplified DNA sample with known copy numbers of the regions amplified, wherein a difference between the two curves indicates a difference in the copy number of at least one amplified region.

2. The method of claim 1, further comprising one or more of:
(a) limiting a total number of amplification cycles prior to plateau of the reaction; or
(b) limiting an amount of polymerase present during amplification sufficient to reduce amplification of the at least two regions.

3. The method of claim 2, wherein the amplification cycles are limited to be about at a cycle at which an amplified region of interest is distinguishable from background noise also generated during the amplification.

4. The method of claim 1, wherein one of the amplified regions is a reference region with the same copy number between samples, and at least one other region is a region of interest that may vary in copy number between samples.

5. The method of claim 1, wherein the concentration of one or more deoxyribonucleotide triphosphates present during amplification is 3.1 µM to 50 µM.

6. The method of claim 1, wherein generating a melting curve comprises collecting fluorescence versus temperature data and wherein the melting curve data is plotted as a negative derivative plot to reveal the amplified regions as melting peaks.

7. The method of claim 6, further comprising normalizing the intensity of the reference peaks between samples such that the intensity of the reference peaks is the same between all samples.

8. The method of claim 6, further normalizing the position of the reference peaks between samples such that all reference peaks are at the same temperature.

9. The method of claim 6, wherein the fluorescence is generated by a saturating dye, by an unsaturating dye, or by a labeled probe.

10. The method of claim 1, wherein the relative copy number of the CNV is quantified.

11. The method of claim 1, wherein the nucleic acid sample comprises fetal DNA and the CNV is associated with a genetic disease or birth defect.

12. The method of claim 11, wherein the fetal DNA is from maternal serum.

13. The method of claim 1, wherein the nucleic acid sample comprises tissue suspected to be cancerous and the CNV is indicative of cancer presence, type, prognosis or therapeutic options.

14. The method of claim 1, wherein one of the amplified regions is a reference region with the same copy number between samples, and at least one other region is a region of interest that may vary in copy number between samples, and wherein the region of interest comprises a portion of a Chemokine (C—C motif) ligand 3-like 1 (CCL3L1) gene of a patient and the copy number is indicative of susceptibility of the patient to Human Immunodeficiency Virus (HIV).

15. The method of claim 1, wherein the nucleic acid sample comprises virally infected tissue and the copy number is used as a means to assess a titer of the virus.

16. A method of determining relative expression levels of a region of interest in nucleic acid samples, the method comprising:
amplifying the region of interest and a reference nucleic acid in each sample while limiting amplification by limiting a concentration of one or more of deoxyribonucleotide triphosphates (dNTPs) without limiting primer concentration present during amplification sufficient to reduce amplification of the region of interest and to maintain the ratio of the region of interest to the reference nucleic acid as amplification reaches plateau, regardless of initial concentration of said region of interest;
generating a melting curve of the region of interest and a melting curve of the reference nucleic acid for each sample;

converting the melting curve of the region of interest to a melting peak of the region of interest and converting the melting curve of the reference nucleic acid to a melting peak of the reference nucleic acid for each sample;

normalizing fluorescence intensity of the reference peaks across the samples, and comparing the melting peak of the region of interest between the samples, wherein a difference between peaks indicates a difference in relative expression levels between the samples.

17. The method of claim 16, wherein the nucleic acid samples comprise messenger ribonucleic acids (mRNA).

18. A method of analyzing nucleic acid amplification melting temperature data from a plurality of mixtures, the method comprising:

amplifying each mixture regardless of initial nucleic acid concentration, each mixture comprising a nucleic acid sample having a region of interest and a reference nucleic acid, to generate a nucleic acid amplicon and a reference amplicon, wherein the amplifying is performed while limiting a concentration of one or more of deoxyribonucleotide triphosphates (dNTPs) without limiting primer concentration in an amount sufficient to reduce amplification of the region of interest;

melting the amplicons to acquire raw fluorescence versus temperature data;

removing background noise from the raw fluorescence versus temperature data;

generating melting peaks for each of the nucleic acid amplicon and the reference amplicon, and normalizing the reference melting peaks for each mixture to the same height to compare the heights of the nucleic acid sample peaks.

19. The method of claim 18, further comprising quantifying relative copy number by locating target peaks of the normalized curves, performing a least squares fit, and calculating the ratios of the peak heights or areas.

20. A method for determining the allele fraction of an allele by performing allele specific amplification on a nucleic acid target in a plurality of samples comprising the nucleic acid target and a reference nucleic acid, the method comprising:

amplifying the allele and the reference nucleic acid in each sample, regardless of the initial allele and nucleic acid concentration, wherein each sample further comprises a pair of primers for amplifying the allele wherein one of the pair of primers is configured to amplify only the allele and the pair of primers is configured to generate an amplicon of the allele, the amplicon having a Tm, a second set of primers configured to produce an amplicon of the reference nucleic acid, wherein a Tm of the amplicon of the reference nucleic acid is different from the Tm of the amplicon of the allele, a polymerase, and dNTPs wherein one or more of dNTPs prior to initiating amplification is limited to about 50% or less of a standard PCR protocol concentration without limiting primer concentration, generating a melting curve of each of the amplicons generated in the amplifying step;

normalizing the melting curves for each reference amplicon across the plurality of samples; and comparing the melting curves of the target amplicons in each sample to determine the allele fraction in each sample.

21. The method of claim 18, wherein removing the background noise comprises performing exponential background subtraction.

* * * * *

SEQUENCE LISTING

<160> NUMBER OF SEQ ID NOS: 29

<210> SEQ ID NO 1
<211> LENGTH: 25
<212> TYPE: DNA
<213> ORGANISM: HoJo virus

<400> SEQUENCE: 1
ttgtgattac ctcagaaatg attga                                          25

<210> SEQ ID NO 2
<211> LENGTH: 20
<212> TYPE: DNA
<213> ORGANISM: HoJo virus

<400> SEQUENCE: 2
cattgcttct tcccagcagt                                                20

<210> SEQ ID NO 3
<211> LENGTH: 20
<212> TYPE: DNA
<213> ORGANISM: HoJo virus

<400> SEQUENCE: 3
aacgggaggg gtgtatgttt                                                20

```
<210> SEQ ID NO 4
<211> LENGTH: 20
<212> TYPE: DNA
<213> ORGANISM: HoJo virus

<400> SEQUENCE: 4
gcagactagg tgcccaactt                                               20

<210> SEQ ID NO 5
<211> LENGTH: 20
<212> TYPE: DNA
<213> ORGANISM: HoJo virus

<400> SEQUENCE: 5
acatcattcc actgggaagc                                               20

<210> SEQ ID NO 6
<211> LENGTH: 20
<212> TYPE: DNA
<213> ORGANISM: HoJo virus

<400> SEQUENCE: 6
ccagagtggg tgcattagga                                               20

<210> SEQ ID NO 7
<211> LENGTH: 20
<212> TYPE: DNA
<213> ORGANISM: HoJo virus

<400> SEQUENCE: 7
tcagacttgg acagccacac                                               20

<210> SEQ ID NO 8
<211> LENGTH: 21
<212> TYPE: DNA
<213> ORGANISM: HoJo virus

<400> SEQUENCE: 8
cacttgggga attgactcac a                                             21

<210> SEQ ID NO 9
<211> LENGTH: 20
<212> TYPE: DNA
<213> ORGANISM: HoJo virus

<400> SEQUENCE: 9
ccttcaggat agcggttgat                                               20

<210> SEQ ID NO 10
<211> LENGTH: 20
<212> TYPE: DNA
<213> ORGANISM: HoJo virus

<400> SEQUENCE: 10
cttgagaatg gatgcgaagg                                               20

<210> SEQ ID NO 11
<211> LENGTH: 21
<212> TYPE: DNA
<213> ORGANISM: HoJo virus

<400> SEQUENCE: 11
caacaggttg tacagggatg a                                             21
```

<210> SEQ ID NO 12
<211> LENGTH: 20
<212> TYPE: DNA
<213> ORGANISM: HoJo virus

<400> SEQUENCE: 12
agctggtgct ccattcttga                                            20

<210> SEQ ID NO 13
<211> LENGTH: 20
<212> TYPE: DNA
<213> ORGANISM: HoJo virus

<400> SEQUENCE: 13
ctcctcatgg ggctaatctg                                            20

<210> SEQ ID NO 14
<211> LENGTH: 20
<212> TYPE: DNA
<213> ORGANISM: HoJo virus

<400> SEQUENCE: 14
aagtccacag aaggcagacg                                            20

<210> SEQ ID NO 15
<211> LENGTH: 20
<212> TYPE: DNA
<213> ORGANISM: HoJo virus

<400> SEQUENCE: 15
agccaggttc ttctcatcca                                            20

<210> SEQ ID NO 16
<211> LENGTH: 20
<212> TYPE: DNA
<213> ORGANISM: HoJo virus

<400> SEQUENCE: 16
gccaggacgt ctgaagaaag                                            20

<210> SEQ ID NO 17
<211> LENGTH: 23
<212> TYPE: DNA
<213> ORGANISM: HoJo virus

<400> SEQUENCE: 17
tctgttgatt ctgctgacaa tct                                        23

<210> SEQ ID NO 18
<211> LENGTH: 24
<212> TYPE: DNA
<213> ORGANISM: HoJo virus

<400> SEQUENCE: 18
tgaacatacc tttccaattt ttca                                       24

<210> SEQ ID NO 19
<211> LENGTH: 20
<212> TYPE: DNA
<213> ORGANISM: HoJo virus

<400> SEQUENCE: 19
gggatagaga gctggcttca                                              20

<210> SEQ ID NO 20
<211> LENGTH: 20
<212> TYPE: DNA
<213> ORGANISM: HoJo virus

<400> SEQUENCE: 20
gccgaagggc attaatgagt                                              20

<210> SEQ ID NO 21
<211> LENGTH: 20
<212> TYPE: DNA
<213> ORGANISM: HoJo virus

<400> SEQUENCE: 21
atgtccggga acacaaagac                                              20

<210> SEQ ID NO 22
<211> LENGTH: 21
<212> TYPE: DNA
<213> ORGANISM: HoJo virus

<400> SEQUENCE: 22
tcccttccct gattaccttt g                                            21

<210> SEQ ID NO 23
<211> LENGTH: 17
<212> TYPE: DNA
<213> ORGANISM: HoJo virus

<400> SEQUENCE: 23
ccctccgaca gggtgaa                                                 17

<210> SEQ ID NO 24
<211> LENGTH: 20
<212> TYPE: DNA
<213> ORGANISM: HoJo virus

<400> SEQUENCE: 24
agcaaatgtc ccatgtcaac                                              20

<210> SEQ ID NO 25
<211> LENGTH: 21
<212> TYPE: DNA
<213> ORGANISM: HoJo virus

<400> SEQUENCE: 25
tcattctcgt tttctgaact g                                            21

<210> SEQ ID NO 26
<211> LENGTH: 20
<212> TYPE: DNA
<213> ORGANISM: HoJo virus

<400> SEQUENCE: 26
atgtttagac tggatagcgt                                              20

<210> SEQ ID NO 27
<211> LENGTH: 25
<212> TYPE: DNA
<213> ORGANISM: HoJo virus

<400> SEQUENCE: 27

```
ttcctttatt ttccttacag ggttt                                            25

<210> SEQ ID NO 28
<211> LENGTH: 25
<212> TYPE: DNA
<213> ORGANISM: HoJo virus

<400> SEQUENCE: 28
ccttccttct ttttgatttt gtctg                                            25

<210> SEQ ID NO 29
<211> LENGTH: 25
<212> TYPE: DNA
<213> ORGANISM: HoJo virus

<400> SEQUENCE: 29
ccttccttct ttttgatttt gtcta                                            25
```